(12) United States Patent
Jia et al.

(10) Patent No.: US 10,526,422 B2
(45) Date of Patent: Jan. 7, 2020

(54) PROCESS FOR PREPARATION AND PURIFICATION OF SUGAMMADES SODIUM

(71) Applicant: Beijing Creatron Institute of Pharmaceutical Research Co., Ltd., Beijing (CN)

(72) Inventors: Huijuan Jia, Beijing (CN); Yan Chen, Beijing (CN); Xiangwei Liu, Beijing (CN)

(73) Assignee: BEIJING CREATRON INSTITUTE OF PHARMACEUTICAL RESEARCH CO., LTD., Beijing (CN)

( * ) Notice: Subject to any disclaimer, the term of this patent is extended or adjusted under 35 U.S.C. 154(b) by 0 days.

(21) Appl. No.: 15/909,824

(22) Filed: Mar. 1, 2018

(65) Prior Publication Data

US 2018/0251575 A1    Sep. 6, 2018

Related U.S. Application Data

(63) Continuation-in-part of application No. 15/544,226, filed as application No. PCT/CN2016/095985 on Aug. 19, 2016, now abandoned.

(30) Foreign Application Priority Data

Jun. 29, 2016 (CN) .......................... 2016 1 0498672

(51) Int. Cl.
  *C08B 37/16* (2006.01)
(52) U.S. Cl.
  CPC ...... *C08B 37/0012* (2013.01); *C07B 2200/13* (2013.01)
(58) Field of Classification Search
  None
  See application file for complete search history.

(56) References Cited

U.S. PATENT DOCUMENTS

| | | | |
|---|---|---|---|
| 6,670,340 B1 | 12/2003 | Zhang et al. | |
| 2004/0029833 A1* | 2/2004 | Zhang | A61K 31/724 514/58 |

FOREIGN PATENT DOCUMENTS

| | | |
|---|---|---|
| CN | 1402737 A | 3/2003 |
| CN | 104628891 A | 5/2015 |
| CN | 104844732 A | 8/2015 |
| WO | 2001/40316 A1 | 6/2001 |
| WO | 2012/025937 A1 | 3/2012 |
| WO | 2014/125501 A1 | 8/2014 |

OTHER PUBLICATIONS

International Search Report and written opinion of the International Searching Authority (in Chinese), dated Apr. 10, 2017, for International Application No. PCT/CN2016/095985, 10 pages.
Extended European Search Report, dated Mar. 22, 2019, for corresponding European Patent Application No. 16865579.3, 5 pages.

* cited by examiner

*Primary Examiner* — Layla D Berry
(74) *Attorney, Agent, or Firm* — Seed IP Law Group LLP

(57) ABSTRACT

The present invention provides a process for the preparation of (6-per-deoxy-6-per-(2-carboxyethyl)thio-γ-cyclodextrin) sodium salt, comprising the steps of:
  reacting γ-cyclodextrin (SM1) with iodine in the presence of triphenylphosphine in an organic solvent to afford an intermediate, 6-per-deoxy-6-iodo-γ-cyclodextrin (abbreviated as SGMD-1);
  adding methanol solution of sodium methoxide into the reaction system followed by the addition of acetone without removal of the solvent under reduced pressure to obtain the crude SGMD-1 as a solid after filtration;
  purifying the crude SGMD-1 by recrystallization;
  reacting a obtained recrystallized intermediate (SGMD-1) with 3-mercaptopropionic acid in basic medium e.g., sodium hydride, to obtain the crude 6-per-deoxy-6-per-(2-carboxyethyl)thio-γ-cyclodextrin sodium salt (abbreviated as SGMD);
  purifying the crude SGMD by passing through adsorbents followed by recrystallization.

40 Claims, 24 Drawing Sheets

Compound Table

| Compound Label | RT | Mass | Abund | Formula | Tgt Mass | Diff (PPM) |
|---|---|---|---|---|---|---|
| Cpd 1: 20.201 | 20.201 | 2175.6354 | 21284 | C48 H72 18 O32 | 2175.6364 | -0.48 |

| Compound Label | m/z | RT | Algorithm | Mass |
|---|---|---|---|---|
| Cpd 1: 20.201 | 2198.6249 | 20.201 | Find by Formula | 2175.6354 |

MS Spectrum

MS Zoomed Spectrum

End Of Report

Qualitative Analysis Report

Peak List

| m/z | z | Abund. | Formula | Ion | Difference(ppm) | Abs Diff(ppm) |
|---|---|---|---|---|---|---|
| 117.00161 | | 1853 | | | | |
| 1999.41432 | 1 | 19055 | C72H111O48S8 | (M-H)- | -6.36 | 6.36 |
| 2000.41805 | 1 | 16730 | C72H111O48S8 | (M-H)- | | |
| 2001.4162 | 1 | 16164 | C72H111O48S8 | (M-H)- | | |
| 2002.41518 | 1 | 9237 | C72H111O48S8 | (M-H)- | | |
| 2003.41534 | 1 | 4838 | C72H111O48S8 | (M-H)- | | |
| 2004.41471 | 1 | 2198 | C72H111O48S8 | (M-H)- | | |
| 2021.39545 | 1 | 2991 | | | | |
| 2022.39734 | 1 | 2641 | | | | |
| 2023.39918 | 1 | 2504 | | | | |

--- End Of Report ---

*FIG. 4C*

```
===========================================================
                    Area Percent Report
===========================================================

Sorted By        :      Signal
Multiplier       :      1.0000
Dilution         :      1.0000
Do not use Multiplier & Dilution Factor with ISTDs Signal 1: MWD1 A, Sig=200,4 Ref=off Peak RetTime Type  Width     Area        Height      Area
 #   [min]         [min]     [mAU*s]     [mAU]       %
----|-------|----|--------|-----------|-----------|--------|
  1   2.203 BV   0.0574      4.44557    1.25289    0.0236
  2   3.504 BB   0.0825      2.27795  3.87735e-1   0.0121
  3  12.216 VB   0.0906      2.42004  3.78307e-1   0.0129
  4  12.849 BV   0.0849      5.34483  9.90948e-1   0.0284
  5  13.012 VB   0.0864      7.75260    1.36191    0.0412
  6  13.308 BV   0.0920      7.85308    1.27320    0.0417
  7  13.570 VB   0.0836      4.14515  7.85528e-1   0.0220
  8  14.049 BB   0.0858     70.87528   12.95272    0.3765
  9  15.522 BB   0.0892     43.59873    7.56791    0.2316
 10  16.201 BV   0.0866    895.89325  161.89049    4.7592
 11  17.209 VV   0.0836      4.71547  8.38175e-1   0.0250
 12  17.324 VB   0.0922      1.96209  2.71854e-1   0.0104
 13  18.349 BV   0.1267   1.77018e4   2227.27832  94.0368
 14  19.121 VV   0.1085      2.83753  3.57770e-1   0.0151
 15  19.284 VB   0.0995      2.24670  3.56701e-1   0.0119
 16  20.892 BV   0.0770      2.38857  4.56620e-1   0.0127
 17  21.037 VV   0.0928     14.45535    2.45006    0.0768
 18  21.500 BB   0.0985      2.96534  4.64415e-1   0.0158
 19  21.856 BV   0.1112      5.34324  7.49215e-1   0.0284
 20  22.046 VB   0.1152      6.04571  7.56979e-1   0.0321
```

*FIG. 5B*

```
Peak RetTime Type  Width     Area      Height      Area
 #   [min]        [min]     [mAU*s]     [mAU]        %
----|-------|----|-------|----------|----------|--------|
 21  23.402 BB   0.0828    4.93259  9.16489e-1  0.0262
 22  23.689 BB   0.0891    4.59034  7.98360e-1  0.0244
 23  24.748 VV   0.1178   13.76730    1.64307   0.0731
 24  26.174 BV   0.0934    7.46356    1.18703   0.0396
 25  28.369 BB   0.1201    4.20189  5.10120e-1  0.0223

Totals :                  1.88243e4  2427.87679
```

============================================================
* End of Report *

*FIG. 5C*

```
===========================================================
                    Area Percent Report
===========================================================

Sorted By           :      Signal
Multiplier          :      1.0000
Dilution            :      1.0000
Do not use Multiplier & Dilution Factor with ISTDs Signal 1: MWD1 A, Sig=200,4 Ref=off Peak RetTime Type  Width     Area      Height     Area
 #   [min]         [min]    [mAU*s]    [mAU]       %
----|-------|----|--------|----------|----------|--------|
  1   2.183 BB   0.0526    3.01733  9.12255e-1   0.0324
  2   3.768 VB   0.0646   28.22783     6.78080   0.3035
  3  12.179 BV   0.0982    7.94321     1.21633   0.0854
  4  12.313 VB   0.0930    1.97615  3.15987e-1   0.0212
  5  12.960 BB   0.1072    2.47090  3.64164e-1   0.0266
  6  13.245 BV   0.1227    1.68854  1.99568e-1   0.0182
  7  13.994 BB   0.0878   30.30825     5.37296   0.3259
  8  14.587 BV   0.0943    3.16750  5.10845e-1   0.0341
  9  14.879 VB   0.0816    1.81964  3.33796e-1   0.0196
 10  15.160 BB   0.0843    3.19482  5.79995e-1   0.0344
 11  15.479 BB   0.0908   33.64925     5.70450   0.3618
 12  15.772 BV   0.0813    2.47334  4.86950e-1   0.0266
 13  16.173 VB   0.0870  329.63629    59.19881   3.5444
 14  17.000 BV   0.0799    2.57946  5.02758e-1   0.0277
 15  17.178 VB   0.0814   43.49159     8.25756   0.4676
 16  18.076 VB   0.0930    4.48286  7.16752e-1   0.0482
 17  18.354 BV   0.0988 8688.51855  1355.14392  93.4238
 18  18.900 VV   0.1520    4.23852  3.58430e-1   0.0456
 19  19.223 VB   0.0838   27.99390     5.11918   0.3010
 20  20.306 BB   0.0938    6.12545  9.94927e-1   0.0659
```

FIG. 6B

| Peak # | RetTime [min] | Type | Width [min] | Area [mAU*s] | Height [mAU] | Area % |
|---|---|---|---|---|---|---|
| 21 | 20.979 | BV | 0.0851 | 1.60992 | 2.88344e-1 | 0.0173 |
| 22 | 21.584 | VV | 0.0914 | 3.46908 | 5.83127e-1 | 0.0373 |
| 23 | 21.808 | VB | 0.0889 | 20.52491 | 3.58051 | 0.2207 |
| 24 | 23.357 | BB | 0.0932 | 6.41659 | 1.08189 | 0.0690 |
| 25 | 23.726 | BB | 0.1545 | 3.78799 | 3.19187e-1 | 0.0407 |
| 26 | 24.622 | BB | 0.1353 | 1.68931 | 1.94622e-1 | 0.0182 |
| 27 | 26.121 | BB | 0.1536 | 2.01578 | 1.84251e-1 | 0.0217 |
| 28 | 28.320 | BB | 0.1040 | 1.83208 | 2.54504e-1 | 0.0197 |
| 29 | 30.289 | BB | 0.0666 | 19.36626 | 4.46841 | 0.2082 |
| 30 | 31.332 | BB | 0.0659 | 2.42329 | 5.44697e-1 | 0.0261 |
| 31 | 32.091 | BB | 0.0564 | 6.50845 | 1.79284 | 0.0700 |
| 32 | 32.525 | BB | 0.0590 | 3.46547 | 8.98345e-1 | 0.0373 |

Totals :                      9300.11252  1467.26121

===================================================================

* End of Report *

FIG. 6C

```
===========================================================
                    Area Percent Report
===========================================================

Sorted By        :      Signal
Multiplier       :      1.0000
Dilution         :      1.0000
Do not use Multiplier & Dilution Factor with ISTDs Signal 1: MWD1 A, Sig=200,4 Ref=off Peak RetTime Type  Width     Area      Height     Area
  #   [min]        [min]    [mAU*s]    [mAU]       %
----|-------|----|-------|----------|----------|--------|
  1   2.191 BBA  0.0518    2.09477  6.45840e-1  0.0227
  2   3.196 BB   0.0561    9.95216  2.75900     0.1079
  3   3.502 BB   0.0800 9.33048e-1  1.75597e-1  0.0101
  4   3.799 BB   0.0653   29.00229  6.86703     0.3145
  5   9.988 BB   0.0761 9.06019e-1  1.64878e-1  9.826e-3
  6  10.384 BV   0.1036    1.06501  1.48582e-1  0.0116
  7  11.461 BB   0.1175    1.47190  1.62693e-1  0.0160
  8  11.666 BB   0.0845 9.40859e-1  1.70051e-1  0.0102
  9  12.362 BB   0.0955 9.25975e-1  1.55519e-1  0.0100
 10  12.617 BV   0.0941    9.97146  1.57080     0.1081
 11  12.791 VB   0.1239    3.83090  4.47177e-1  0.0415
 12  13.404 BB   0.1056    2.82164  4.13426e-1  0.0306
 13  13.668 BV   0.1224    1.57171  1.69163e-1  0.0170
 14  14.402 BB   0.0870   44.06052  7.90384     0.4778
 15  15.000 BV   0.1051    3.81151  5.34845e-1  0.0413
 16  15.240 VB   0.0924    1.02247  1.64708e-1  0.0111
 17  15.519 BB   0.1000    1.46358  2.30723e-1  0.0159
 18  15.862 BV   0.0898   50.33568  8.66470     0.5459
 19  16.114 VV   0.1140    1.79861  2.28085e-1  0.0195
 20  16.346 VV   0.0903    1.26326  2.22211e-1  0.0137
```

*FIG. 7B*

| Peak # | RetTime [min] | Type | Width [min] | Area [mAU*s] | Height [mAU] | Area % |
|---|---|---|---|---|---|---|
| 21 | 16.539 | VB | 0.0898 | 293.62354 | 52.04633 | 3.1844 |
| 22 | 17.366 | BV | 0.0761 | 1.11490 | 2.16605e-1 | 0.0121 |
| 23 | 17.547 | VV | 0.0841 | 24.36884 | 4.43740 | 0.2643 |
| 24 | 18.067 | BV | 0.0925 | 1.43937 | 2.31541e-1 | 0.0156 |
| 25 | 18.239 | VV | 0.0851 | 1.37641 | 2.25795e-1 | 0.0149 |
| 26 | 18.373 | VV | 0.0746 | 1.18236 | 2.27548e-1 | 0.0128 |
| 27 | 18.485 | VB | 0.0921 | 2.00103 | 3.42864e-1 | 0.0217 |
| 28 | 18.759 | BB | 0.1008 | 8646.90820 | 1349.51123 | 93.7770 |
| 29 | 19.616 | BB | 0.0852 | 18.00414 | 3.32123 | 0.1953 |
| 30 | 20.713 | BB | 0.0866 | 2.41889 | 3.99761e-1 | 0.0262 |
| 31 | 21.835 | BV | 0.1295 | 1.62697 | 1.83322e-1 | 0.0176 |
| 32 | 21.995 | VV | 0.0897 | 3.28981 | 5.20897e-1 | 0.0357 |
| 33 | 22.211 | VB | 0.0926 | 14.14153 | 2.40389 | 0.1534 |
| 34 | 23.777 | VB | 0.0911 | 5.45434 | 9.47808e-1 | 0.0592 |
| 35 | 24.086 | BV | 0.0806 | 1.91003 | 3.34421e-1 | 0.0207 |
| 36 | 24.186 | VV | 0.1142 | 2.61467 | 3.53949e-1 | 0.0284 |
| 37 | 24.463 | VB | 0.1098 | 9.62781e-1 | 1.17252e-1 | 0.0104 |
| 38 | 25.067 | BV | 0.1170 | 2.26360 | 2.90279e-1 | 0.0245 |
| 39 | 25.969 | BB | 0.0792 | 1.14332 | 2.04668e-1 | 0.0124 |
| 40 | 26.576 | BB | 0.1022 | 5.33062 | 7.94894e-1 | 0.0578 |
| 41 | 28.041 | BB | 0.0855 | 1.02865 | 1.67823e-1 | 0.0112 |
| 42 | 28.775 | BB | 0.0971 | 5.53649 | 8.60159e-1 | 0.0600 |
| 43 | 30.514 | BB | 0.0677 | 4.33555 | 1.01770 | 0.0470 |
| 44 | 31.472 | BB | 0.0589 | 5.48569 | 1.49012 | 0.0595 |
| 45 | 32.208 | BB | 0.0572 | 2.97788 | 8.03816e-1 | 0.0323 |
| 46 | 32.634 | BB | 0.0633 | 9.25278e-1 | 2.18804e-1 | 0.0100 |

Totals :       9220.70828  1453.46898

\*\*\* End of Report \*\*\*

*FIG. 7C*

```
===========================================================
                    Area Percent Report
===========================================================

Sorted By        :      Signal
Multiplier       :      1.0000
Dilution         :      1.0000
Do not use Multiplier & Dilution Factor with ISTDs Signal 1: MWD1 A, Sig=200,4 Ref=off Peak  RetTime Type  Width     Area       Height       Area
 #     [min]        [min]    [mAU*s]     [mAU]         %
----|-------|----|-------|----------|----------|--------|
  1   2.190 BBA   0.0510    2.11716  6.67965e-1   0.0224
  2   3.201 BB    0.0582   15.92674     4.39896   0.1684
  3   3.803 BB    0.0677   29.44279     6.90618   0.3114
  4   9.961 BB    0.1325    1.04389  1.06344e-1   0.0110
  5  11.607 BB    0.1113    1.08671  1.30269e-1   0.0115
  6  12.563 BV    0.1068    7.23503     1.01890   0.0765
  7  12.727 VB    0.0991    2.33745  3.20262e-1   0.0247
  8  13.357 VB    0.1222    2.19373  2.90089e-1   0.0232
  9  14.349 BB    0.0873   24.61710     4.39595   0.2603
 10  14.951 BV    0.0943    3.19367  5.15485e-1   0.0338
 11  15.081 VV    0.0787 9.69480e-1 1.69671e-1   0.0103
 12  15.201 VB    0.0783    1.19779  2.17420e-1   0.0127
 13  15.499 BB    0.0950    1.93520  3.27146e-1   0.0205
 14  15.844 BV    0.0917   27.73581     4.64034   0.2933
 15  16.107 VV    0.1085    2.61451  3.69714e-1   0.0276
 16  16.339 VV    0.0810    1.63239  2.93024e-1   0.0173
 17  16.534 VB    0.0884  255.87799    44.96633   2.7060
 18  17.374 BV    0.0860    1.92040  3.39347e-1   0.0203
 19  17.557 VB    0.0823   33.25457     6.22447   0.3517
 20  18.085 BV    0.0957    1.49363  2.30150e-1   0.0158
```

*FIG. 8B*

| Peak # | RetTime [min] | Type | Width [min] | Area [mAU*s] | Height [mAU] | Area % |
|---|---|---|---|---|---|---|
| 21 | 18.486 | VB | 0.1179 | 4.35459 | 5.29987e-1 | 0.0461 |
| 22 | 18.762 | BB | 0.1018 | 8920.83984 | 1372.98657 | 94.3406 |
| 23 | 19.641 | BB | 0.0824 | 20.31250 | 3.79780 | 0.2148 |
| 24 | 20.471 | BV | 0.1416 | 1.14836 | 1.05002e-1 | 0.0121 |
| 25 | 20.726 | VB | 0.0999 | 3.82448 | 6.03809e-1 | 0.0404 |
| 26 | 21.415 | BV | 0.1313 | 2.64999 | 2.63468e-1 | 0.0280 |
| 27 | 21.624 | VB | 0.0836 | 9.55092e-1 | 1.55722e-1 | 0.0101 |
| 28 | 22.015 | BV | 0.1068 | 3.65956 | 5.15944e-1 | 0.0387 |
| 29 | 22.234 | VB | 0.0910 | 18.72841 | 3.26282 | 0.1981 |
| 30 | 23.804 | BV | 0.0937 | 17.15048 | 2.86950 | 0.1814 |
| 31 | 24.187 | VB | 0.1394 | 3.57525 | 3.32631e-1 | 0.0378 |
| 32 | 25.065 | BB | 0.1202 | 1.76926 | 2.06093e-1 | 0.0187 |
| 33 | 25.969 | BB | 0.1127 | 1.65095 | 2.12446e-1 | 0.0175 |
| 34 | 26.582 | BB | 0.0897 | 4.01367 | 6.71963e-1 | 0.0424 |
| 35 | 28.793 | BB | 0.1172 | 4.84583 | 6.34067e-1 | 0.0512 |
| 36 | 30.526 | BB | 0.0649 | 9.90162 | 2.36026 | 0.1047 |
| 37 | 31.485 | BB | 0.0773 | 3.31156 | 6.10345e-1 | 0.0350 |
| 38 | 32.219 | BB | 0.0586 | 10.76851 | 2.81983 | 0.1139 |
| 39 | 32.645 | BB | 0.0567 | 3.46358 | 9.46123e-1 | 0.0366 |
| 40 | 34.897 | BB | 0.1093 | 1.24504 | 1.40611e-1 | 0.0132 |

Totals : 9455.99461 1470.55300

\*\*\* End of Report \*\*\*

*FIG. 8C*

```
===========================================================
                     Area Percent Report
===========================================================

Sorted By           :     Signal
Multiplier          :     1.0000
Dilution            :     1.0000
Do not use Multiplier & Dilution Factor with ISTDs Signal 1: DAD1 A, Sig=200,4 Ref=off Peak  RetTime Type  Width     Area        Height       Area
 #    [min]         [min]     [mAU*s]     [mAU]         %
----|-------|----|-------|-----------|-----------|-------|
   1  11.647 VV   0.1234      3.99984  4.88960e-1   0.0216
   2  13.418 BBA  0.0875    107.12428   19.07248    0.5772
   3  13.978 BV   0.0926     10.08461    1.66549    0.0543
   4  14.852 BV   0.0910     76.26088   12.88891    0.4109
   5  15.508 VB   0.0879    884.42426  156.62880    4.7654
   6  16.505 VV   0.0820     25.44579    4.78964    0.1371
   7  17.759 VV   0.1339   1.73709e4  2069.67725   93.5961
   8  18.688 VV   0.0927      8.87618    1.46391    0.0478
   9  20.418 VB   0.0935     15.10677    2.53527    0.0814
  10  21.242 BV   0.0943     37.00066    6.13796    0.1994
  11  22.765 VB   0.0850      3.13927  5.46473e-1   0.0169
  12  24.094 BB   0.1019     17.06814    2.43167    0.0920

Totals :                   1.85594e4  2278.32681
```

Data File F:\SGMD\SGMD\Testing\20170925\S1 2017-09-25 15-24-58\SG22-1.D Sample
Name: SG22-1

* End of Report *

FIG. 9B

```
===================================================================
                        Area Percent Report
===================================================================

Sorted By        :       Signal
Multiplier       :       1.0000
Dilution         :       1.0000
Do not use Multiplier & Dilution Factor with ISTDs Signal 1: DAD1 A, Sig=200,4 Ref=off Peak RetTime Type  Width     Area      Height      Area
 #   [min]         [min]    [mAU*s]    [mAU]        %
----|-------|----|-------|----------|----------|--------|
  1  11.546 VB   0.1022      2.42666 3.62180e-1   0.0132
  2  13.331 BB   0.0880     62.78502  11.10334    0.3410
  3  13.882 BB   0.0879     16.45044   2.91080    0.0893
  4  14.730 BB   0.0895     43.56184   7.52969    0.2366
  5  15.393 BV   0.0887    578.01581 101.12112    3.1390
  6  15.833 VB   0.0924      5.29957 9.04379e-1   0.0288
  7  16.382 BB   0.0788     29.71681   5.89893    0.1614
  8  17.634 VB   0.1416 1.76164e4   2022.97522   95.6686
  9  20.284 VB   0.0940     24.79364   4.13191    0.1346
 10  21.106 BB   0.0920     16.45590   2.82383    0.0894
 11  23.935 BBA  0.0949     18.07712   2.81669    0.0982

Totals :                  1.84140e4   2162.57810

Data File F:\SGMD\SGMD\Testing\20171122\S2 2017-11-22 18-02-01\SG23-1.D Sample
Name: SG23-1

===================================================================
                        * End of Report *
```

FIG. 10B

```
===============================================================
                       Area Percent Report
===============================================================

Sorted By         :      Signal
Multiplier        :      1.0000
Dilution          :      1.0000
Do not use Multiplier & Dilution Factor with ISTDs Signal 1: DAD1 A, Sig=200,4 Ref=off Peak  RetTime Type  Width     Area       Height      Area
 #     [min]        [min]    [mAU*s]      [mAU]       %
----|-------|----|-------|-----------|-----------|--------|
   1  11.640 VB   0.0892     2.24085  4.00962e-1   0.0119
   2  13.397 BV   0.0886    68.05609   11.92106    0.3616
   3  13.966 BV   0.0975    10.56276    1.67659    0.0561
   4  14.827 BV   0.0918    48.38180    8.08329    0.2571
   5  15.475 VV   0.0886   943.10828  165.29311    5.0109
   6  16.451 BV   0.0821    33.10138    6.22146    0.1759
   7  17.703 BV   0.1307  1.76395e4  2172.58691   93.7208
   8  20.364 VB   0.0927    22.58770    3.83626    0.1200
   9  21.192 BV   0.0959    30.00397    4.86726    0.1594
  10  22.709 BB   0.0833     7.79197    1.48249    0.0414
  11  24.027 VF   0.1039    16.00099    2.27879    0.0850

Totals :                   1.88213e4  2378.64818

===============================================================
                       *** End of Report ***
```

FIG. 11B

PROCESS FOR PREPARATION AND PURIFICATION OF SUGAMMADES SODIUM

This application is a continuation-in-part application of U.S. application Ser. No. 15/544,226 filed on Jul. 17, 2017 which is a 371 of International Application No. PCT/CN2016/095985 filed on Aug. 19, 2016 and claims priority to CN Application No. 201610498672.9 filed on Jun. 29, 2016, which is incorporated herein by reference.

FIELD OF THE INVENTION

The present invention belongs to the field of drug synthesis and relates to the preparation of active pharmaceutical ingredients and intermediates. More particularly, the present invention relates to a process for the preparation and purification of Sugammadex sodium and its intermediates.

BACKGROUND OF THE INVENTION

Sugammadex sodium (abbreviated as SGMD) was first discovered by Organon Biosciences. In 2007, Organon Biosciences was acquired by Schering-Plough, the latter merged with Merck & Co. in 2009. SGMD is now owned and sold by Merck & Co. SGMD and its injection were approved by EMEA at the end of 2009, of which the tradename is Bridion. In 2010, SGMD was approved by PMDA and then by FDA in December 2015. Since then, SGMD and its injection have been launched in more than 50 countries all over the world. In 2015, CFDA approved the application of SGMD injection as investigational new drug (IND) by N.V. Organon's.

Sugammadex sodium represents the first and only selective relaxant binding agent (SRBA) and is one of the most notable achievements in the field of anaesthetic during the last 20 years. SGMD chelates free rocuronium bromide molecules thus rapidly reduces the concentration thereof in plasma. The transfer of rocuronium bromide molecule from neuromuscular junction to plasma caused by the concentration difference between them renders in the decrease of the concentration of rocuronium bromide molecule at neuromuscular junction so that rocuronium bromide molecule bound to nicotinic acetylcholine receptors (nAChRs) is released at neuromuscular junction which results in the reversal of neuromuscular blockade induced by rocuronium bromide molecule.

Sugammadex sodium binds to and inactivates non-polarizing muscle relaxants with high selectivity. It antagonizes rocuronium bromide molecule due to the chelating between the lipophilic core of SGMD and the rocuronium bromide molecules. The similar antagonism works also to vecuronium bromide which is an analogue of rocuronium bromide molecule. However, no reversal effect for neither the non-depolarizing muscle relaxants with the structure of benzyl isoqunoline e.g., cis-atracurium, nor the depolarizing neuromulscular blocking agents e.g., succinylcholine.

Sugammadex sodium is a modified derivative of γ-cyclodextrin which contains 8 glucopyranose units with a lipophilic core and a hydrophilic periphery. The full chemical name of SGMD is 6-per-deoxy-6-per-(2-carboxyethyl)thio-γ-cyclodextrin, sodium salt. Its structure is shown as below:

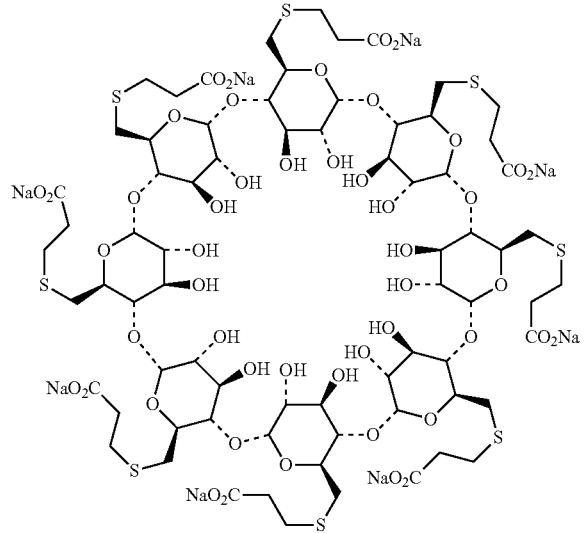

Due to its complex structure, extreme polarity and good water solubility, the preparation and purification of SGMD becomes very difficult since the impurities produced during the preparation thereof have physico-chemical characteristics and molecular weights comparable to that of the active substance. The current existing methods for the preparation of SGMD are as listed as follows:

1. Patent CN1188428C (cognate patent of EP1259550B1) assigned to Akzo Noble, the inventor of Sugammadex sodium.

The process described in this patent started from γ-cyclodextrin, which reacts with iodine and triphenylphosphine to afford an intermediate, 6-per-deoxy-6-iodo-γ-cyclodextrin (SGMD-1). The intermediate SGMD-1 thus prepared reacts with 3-mercaptopropionic acid to provide the crude Sugammadex sodium salt by nucleophilic substitution which was further purified by passing through macroporous resin and dialysis to remove impurities. The preparation of SGMD-1 according to this process requires cooling the reaction system prior to the addition of sodium methoxide and mixing the mixture prior to the addition of methanol and evaporation thereof.

2. Patents WO2012025937 and WO2014125501.

Compared to the route described in the patent CN1188428C, the process in this patent (WO2014125501) employed a different intermediate rather than SGMD-1.

γ-cyclodextrin reacts with phosphorous pentachloride (or phosphorous pentabromide) instead of iodine and triphenylphosphine to afford 6-per-deoxy-6-chloro (or bromo)-γ-cyclodextrin which reacts with 3-mercaptopropionic acid by nucleophilic substitution to afford the crude SGMD which is further purified to obtain SGMD.

The preparation of SGMD described in patent WO2012025937 was same to that in patent WO2014125501, both of them use phosphorous pentahalide instead of iodine and triphenylphosphine used in CN1188428C. This process requires also the evaporation of DMF, a high boiling point organic solvent, at the end of the first step. In the second step, the addition of ethanol to the reaction system will precipitate the product of SGMD as well as the unreacted SGMD-1. Thus the purification requires silica gel and sephadex G25 column chromatography. While in patent WO2014125501, the crude SGMD was purified by recrystallization with methanol, ethanol, acetonitrile and water. Prior to recrystallization, active carbon was added to decolorize the product.

DESCRIPTION OF THE INVENTION

The present invention relates to an industrially viable, cost effective process for the preparation of Sugammadex sodium.

In an embodiment of the present invention, the process described in this invention involves reacting γ-cyclodextrin (SM1) with iodine and triphenylphosphine in an organic solvent to afford an intermediate 1, 6-per-deoxy-6-iodo-γ-cyclodextrin (abbreviated as SGMD-1). After recrystallization, SGMD-1 was treated with 3-mercaptopropionic acid (SM2) in an organic solvent under basic condition to afford the crude 6-per-deoxy-6-per-(2-carboxyethyl)thio-γ-cyclodextrin, sodium salt (abbreviated as SGMD). The crude SGMD was further purified by absorbent and recrystallization.

In an embodiment of the present invention, the present invention provides a process for the preparation of Sugammadex sodium comprising:

reacting γ-cyclodextrin (SM1) with iodine in the presence of triphenylphosphine in an organic solvent to afford an intermediate, 6-per-deoxy-6-iodo-γ-cyclodextrin (SGMD-1);

adding methanol solution of sodium methoxide into the reaction system followed by the addition of acetone without removal of the solvents under reduced pressure to obtain the crude product of SGMD-1 as a solid after filtration;

purifying the crude SGMD-1 by recrystallization;

reacting thus obtained recrystallized intermediate (SGMD-1) with 3-mercaptopropionic acid (SM2) in basic medium e.g., sodium hydride, to obtain a crude product of 6-per-deoxy-6-per-(2-carboxyethyl)thio-γ-cyclodextrin sodium salt (SGMD);

purifying the crude SGMD by passing through adsorbents followed by recrystallization.

In an embodiment of the present invention, the organic solvent is N,N-dimethylformamide.

In an embodiment of the present invention, t process for the preparation of Sugammadex sodium is outlined as follows:

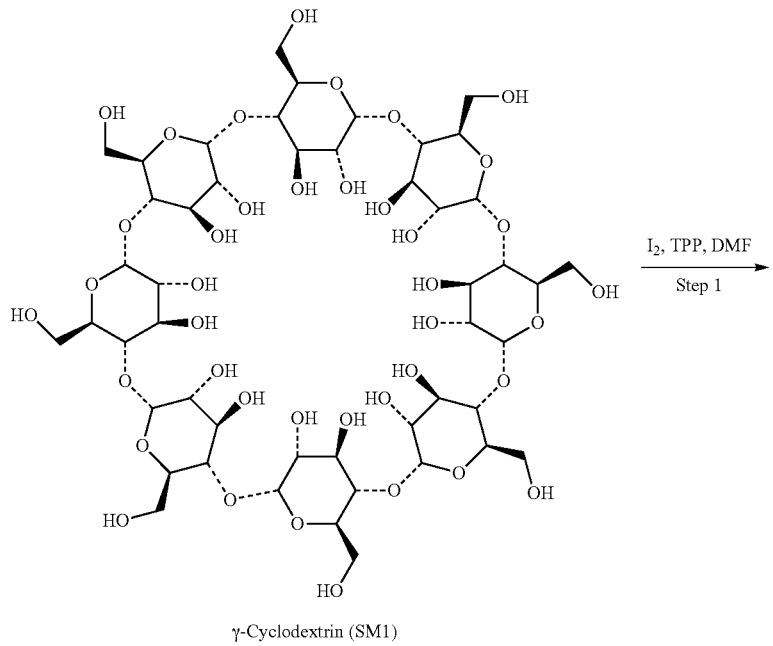

γ-Cyclodextrin (SM1)

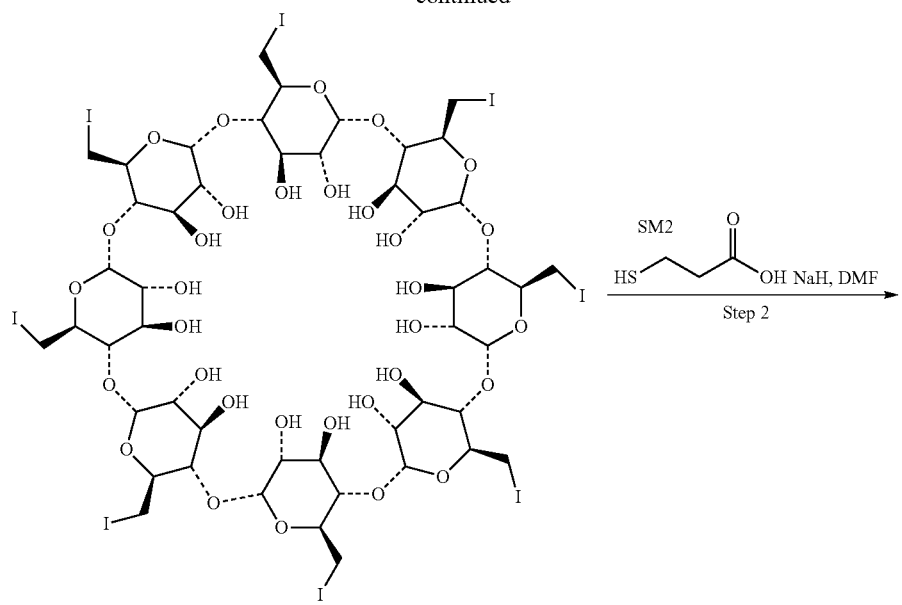
Intermediate of Sugammadex sodium (SGMD-1)
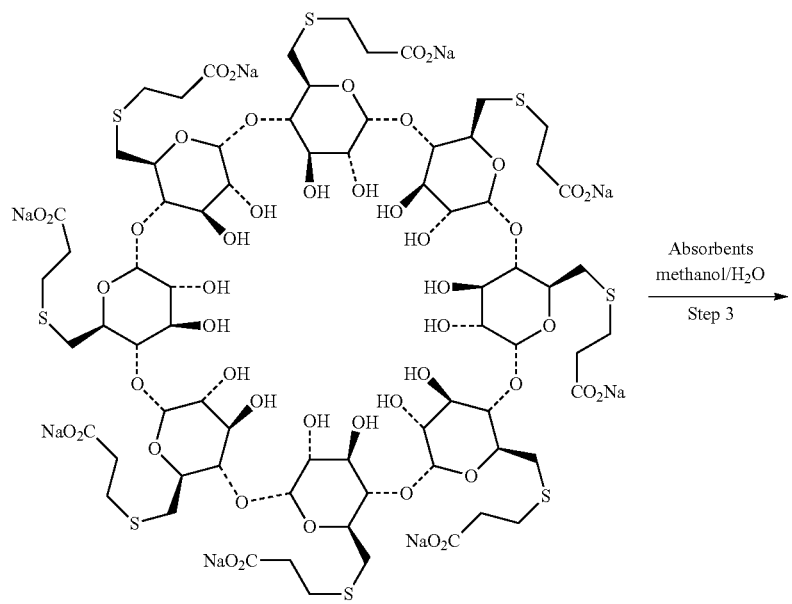
Crude product of Sugammadex sodium (SGMD-CP)

-continued

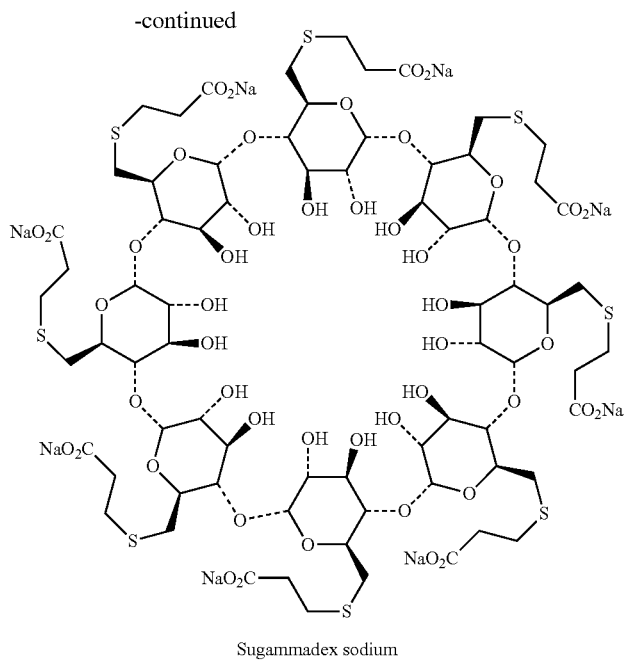

Sugammadex sodium

In an embodiment of the present invention, the ratio (V/W) of acetone and the γ-cyclodextrin (SM1) is 30:1-150:1, preferably 35:1-140:1,40:1-130:1,45:1-120:1,50:1-110:1, 50:1-100:1, and most preferably 60:1-100:1.

In an embodiment of the present invention, the process is characterized in that prior to the preparation of crude SGMD, the obtained intermediate SGMD-1 is precipitated by the addition of acetone to the reaction system which is then purified by recrystallization. Solvent used in the recrystallization of SGMD-1 is dimethylformamide (DMF), dimethyl sulfoxide (DMSO), methanol, ethanol, isopropanol or acetone, or the mixture of the two above solvents, preferably a mixture of acetone and DMF, a mixture of acetone and DMSO, a mixture of methanol and DMF or a mixture of ethanol and DMF, and most preferably a mixture of acetone and DMF. Theratio (V/V) of the mixture of the two above solvents is 1:0.3-1:2.5, preferably 1:0.4-1:2.4, 1:0.5-1:2.3, 1:0.6-1:2.2, 1:0.7-1:2.1, and most preferably 1:0.8-1:2.0.

In an embodiment of the present invention, the process is characterized in that the molar ratio of intermediate 1 (SGMD-1) and 3-mercaptopropionic acid (SM2) is 1:8-1:25, preferably 1:9-1:24,1:10-1:22,1:11-1:21, and most preferably 1:12-1:20.

In an embodiment of the present invention, the process is characterized in that the molar ratio of intermediate 1 (SGMD-1) and sodium hydride is 1:10-1:50, preferably 1:12-1:48,1:15-1:45,1:17-1:42, 1:18-1:40, and most preferably 1:22-1:40.

In an embodiment of the present invention, the process is characterized in that the solvent used in the recrystallization of crude SGMD is ethanol, water, methanol or isopropanol, or a mixture of the two above solvents, preferably a mixture of methanol and water or a mixture of ethanol and water.

In an embodiment of the present invention, the process is characterized in that the adsorbent is active carbon, silica gel, macro porous resin, aluminum oxide (basic aluminum oxide or neutral aluminum oxide), molecular sieves or zeolite, or the combination of 2-3 above adsorbents, preferably the combination of aluminum oxide and active carbon, wherein aluminum oxide and active carbon could be used alone or in combination.

In an embodiment of the present invention, the characteristic of the method is that the ratio (W/W) of crude SGMD and absorbent(s) is 1:0.1-1:2.5, preferably 1:0.1-1:2.3, 1:0.1-1:2.1, 1:0.2-1:2.0 or 1:0.2-1:1.8, and most preferably 1:0.2-1:1.5.

Compared to the prior art, the present invention avoids the influence of triphenylphosphine oxide, a byproduct caused by the reaction between γ-cyclodextrin and iodine in the presence of triphenylphosphineon the following reactions, evaporation of high boiling point solvent DMF so that to simplify the process and improve the quality of SGMD-1. Meanwhile, the process of the present invention is simple and economic by removing impurities from crude SGMD with absorbent(s) and recrystallizing crude SGMD, which can also provide desired Sugammadex sodium salt without new impurities. Therefore, the quality of Sugammadex sodium salt produced by the present process is controllable which is comparable to the quality of the commercially available product.

DESCRIPTION OF DRAWINGS

FIGS. 4A-4C: HRMS of 6-per-deoxy-6-per-(2-carboxyethyl)thio-γ-cyclodextrin Sodium Salt.

FIGS. 5A-5C: Analysis spectrum of the related substances of sugammadex sodium prepared by the process of the present invention.

FIGS. 6A-6C: Analysis spectrum of the related substances of commercially available Injection Bridion 5 ml (batch number; R501G).

FIGS. 7A-7C: Analysis spectrum of the related substances of commercially available Injection Bridion 5 ml (batch number; S217P).

FIGS. 8A-8C: Analysis spectrum of the related substances of commercially available Injection Bridion 5 ml (batch number; S502P).

FIGS. 9A-9B: Analysis spectrum of the related substances of sugammadex sodium (SG22) prepared by the method of the present invention.

FIGS. 10A-10B: Analysis spectrum of the related substances of sugammadex sodium (SG23) prepared by the method of the present invention.

FIGS. 11A-11B: Analysis spectrum of the related substances of sugammadex sodium (SG24) prepared by the method of the present invention.

EMBODIMENTS

Figure 1:
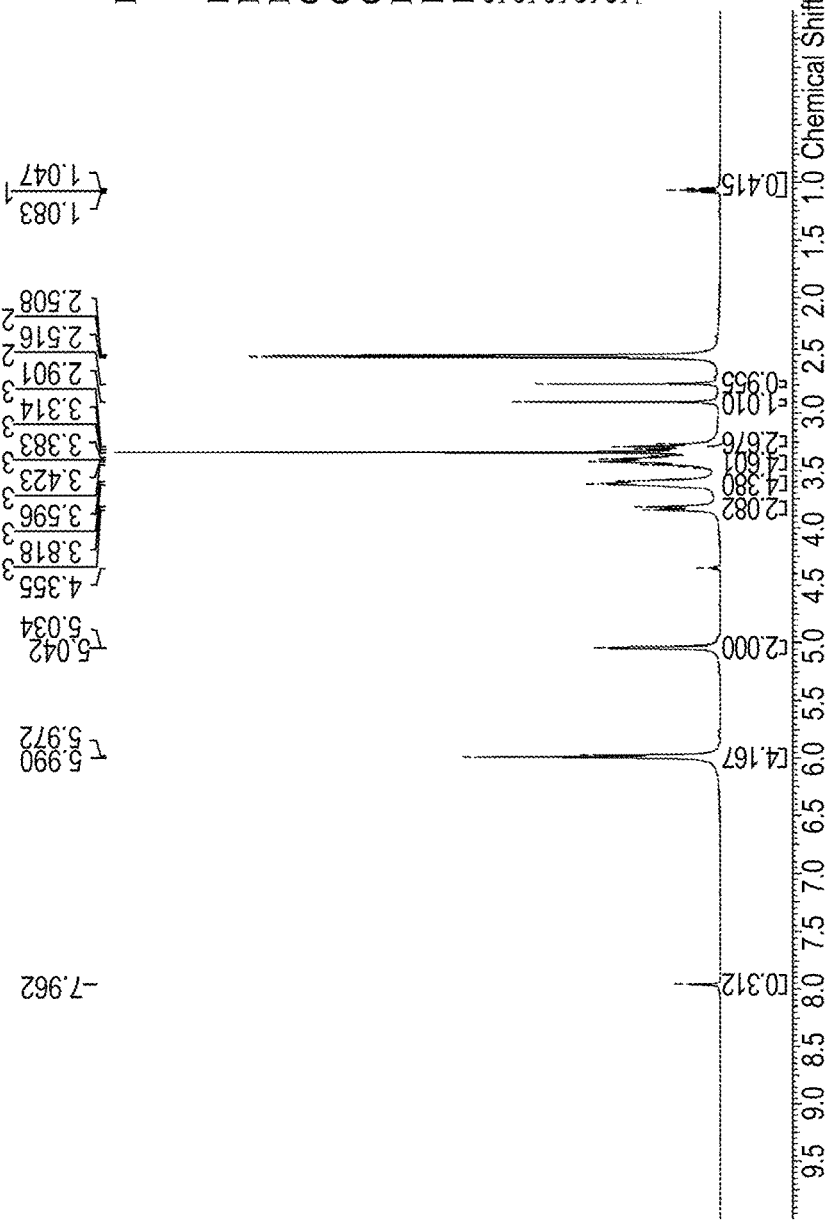
FIG. 1: $^1$H-NMR of 6-per-deoxy-6-per-iodo-γ-cyclodextrin.

Detailed embodiments of the present invention are disclosed herein below. However, it is to be understood that the disclosed embodiments are merely exemplary of the invention. The scope of the invention is not limited to the disclosed embodiments.

Example 1: Preparation of
6-per-deoxy-6-per-iodo-γ-cyclodextrin (SGMD-1)

To a 1 L three-necked flask, dimethyformamide (DMF) (170 g) and triphenylphosphine (36.16 g) were introduced sequentially with stirring under an atmosphere of nitrogen at room temperature. The mixture was stirred till the triphenylphosphine was completely dissolved. To the above mixture was added dropwise a solution of iodine in DMF (36.63 g of iodine in 45 g of DMF). The reaction system was maintained and stirred at 20-30° C. for 30 mins prior to the addition of γ-cyclodextrin (12 g). Then the reaction system was heated to 70° C. and stirred at the same temperature till the starting material was completely consumed (~24 hrs, monitored by HPLC).

The reaction system was cooled down to 20° C. and maintained at 20-30° C., to which a solution of sodium methoxide in methanol (8.74 g of sodium methoxide suspended in 48 g of methanol) was added dropwise. The mixture was stirred for 2 hrs at the same temperature prior to the addition of acetone (995 g) during the course of which solid started to precipitate. The stirring was continued for another 2 hrs. The resultant solid was collected by filtration under reduced pressure, washed with acetone (20 g) and dried at 45-50° C. for 8-13 hrs.

The resultant solid was dissolved in a premixed solvent DMF-acetone (170 g, acetone/DMF=1:0.8, V/V) at 50° C. and stirred for 60 mins at the same temperature. The reaction system was to cooled down to 20-30° C. with stirring. The resultant crystals were filtered, washed with acetone (32 g) and dried under vacuum at 45-50° C. for 8-13 hrs to afford 14.9 g of the entitled compound SGMD-1 as off-white powder. Yield: 69.5%.

Example 2: Preparation of
6-per-deoxy-6-per-iodo-γ-cyclodextrin (SGMD-1)

To a 5 L three-necked flask, dimethylformamide (DMF) (227 g) and triphenylphosphine (36.16 g) were introduced sequentially with stirring under an atmosphere of nitrogen at room temperature. The mixture was stirred till the triphenylphosphine was completely dissolved. To the above mixture was added dropwise a solution of iodine in DMF (36.63 g of iodine in 45 g of DMF). The reaction system was maintained and stirred at 20-30° C. for 30 mins prior to the addition of γ-cyclodextrin (12 g). Then the reaction system was heated to 70° C. and stirred at the same temperature till the starting material was completely consumed (~24 hrs, monitored by HPLC).

The reaction system was cooled down to 20° C. and maintained at 20-30° C., to which sodium methoxide (8.74 g sodium methoxide suspended in 48 g methanol) was added dropwise. The mixture was stirred for 2 hrs at the same temperature prior to the addition of acetone (948 g) during the course of which solid started to precipitate. The stirring was continued for another 2 hrs at 20-30° C. The resultant solid was collected by filtration under reduced pressure, washed with acetone (20 g), and dried at 45-50° C. for 8-13 hrs.

Figure 2:
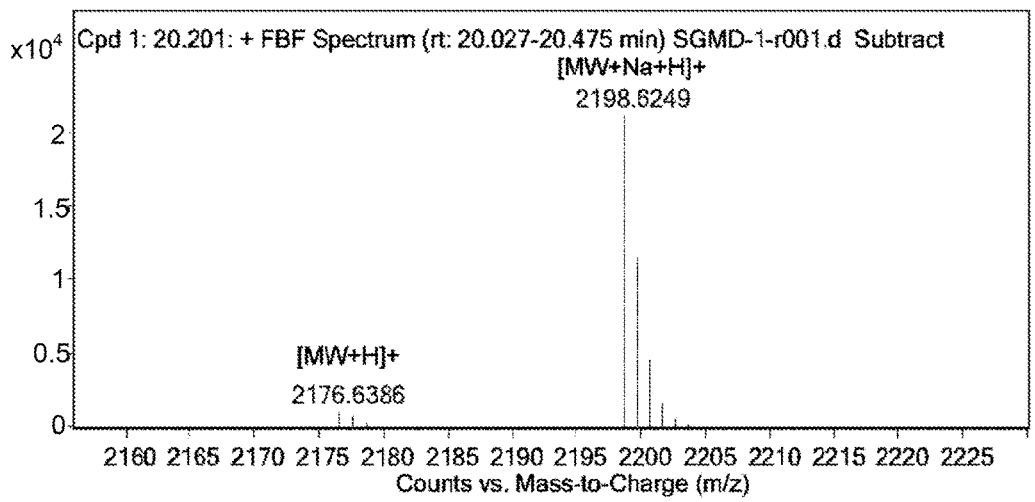
FIG. 2: HRMS of 6-per-deoxy-6-per-iodo-γ-cyclodextrin.
Figure 2:
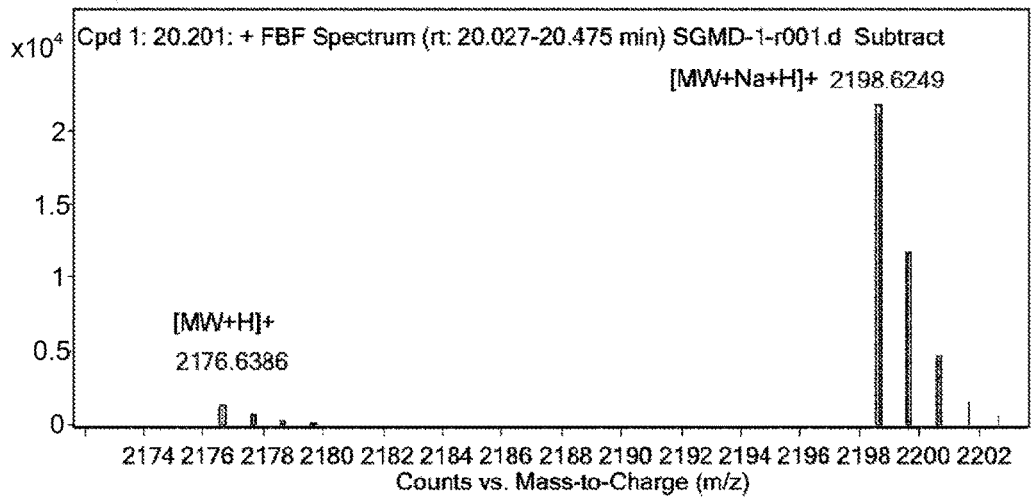

The solid was dissolved in a premixed solvent DMF-acetone (270 g, acetone/DMF=1:1.5, V/V) at 50° C. and stirred for 60 mins at the same temperature. The reaction system was cooled down to 20-30° C. with stirring. The resultant crystals were filtered, washed with acetone (32 g) and dried under vacuum at 45-50° C. for 8-13 hrs to afford 18.72 g of the entitled compound SGMD-1 as off-white powder. Yield: 93.0%. $^1$H-NMR (400 MHz, DMSO-$d_6$) δ: 5.990-5.972 (m, 16H), 5.042-5.034 (d, J=3.2 Hz, 8H), 3.841-3.818 (m, 8H), 3.619 (m, 16H), 3.448-3.423 (m, 8H), 3.340-3.292 (in, 8H) (FIG. 1). ESI-HRMS: found 2176.6386 [M+H]$^+$, 2198.6249 [M+Na+H]$^+$, calcd: 2175.6354 [M+H]$^+$, the absolute error is: 0.48 ppm, the error is acceptable (FIG. 2).

Example 3: Preparation of
6-per-deoxy-6-per-iodo-γ-cyclodextrin (SGMD-1)

To a 1 L three-necked flask, dimethyformamide (DMF) (159 g) and triphenylphosphine (36.16 g) were introduced sequentially with stirring under an atmosphere of nitrogen at the room temperature. The mixture was stirred till the triphenylphosphine was completely dissolved. To the above mixture was added dropwise a solution of iodine in DMF (36.63 g of iodion in 45 g of DMF). The reaction system was maintained and stirred at 20-30° C. for 30 mins prior to the addition of γ-cyclodextrin (12 g). Then the reaction system was heated to 70° C. and stirred at the same temperature till the starting material was completely consumed (~24 hrs, monitored by HPLC).

The reaction system was cooled down to 20° C. and maintained at 20-30° C., to which a solution of sodium methoxide in methanol (8.74 g of sodium methoxide suspended in 48 g of methanol) was added. The mixture was stirred for 2 hrs at the same temperature prior to the addition of acetone (398 g) during the course of which solid started to precipitate. The stirring was continued for another 2 hrs. The resultant solid was collected by filtration under reduced pressure, washed with acetone (20 g) and dried at 45-50° C. under vacuum for 8-13 hrs.

The solid was dissolved in premixed solvent of DMF-acetone (270 g, acetone: DMF=1.0:2.0,V/V) at 50° C. and stirred for 60 mins at the same temperature. The reaction system was cooled down to 20-30° C. with stirring. The resultant crystals were filtered, washed with acetone (32 g) and dried under vacuum at 45-50° C. for 8-13 hrs to afford 17.51 g of the entitled compound SGMD-1 as off-white powder. Yield: 87.0%.

Example 4: Preparation of
6-per-deoxy-6-per-iodo-γ-cyclodextrin (SGMD-1)

To a 50 L three-necked flask, dimethyformamide (DMF) (13.2 kg) and triphenylphosphine (3.6 kg) were introduced sequentially with stirring under an atmosphere of nitrogen. The mixture was stirred till the triphenylphosphine was completely dissolved. To the above mixture was added dropwise a solution of iodine in DMF (3.67 kg iodine in 4.5 kg DMF). The reaction system was maintained and stirred at 20-30° C. for 30 minutes prior to the addition of γ-cyclodextrin (1.2 kg). Then the reaction system was heated to 70° C. and stirred at the same temperature till the starting material was completely consumed (~24 hrs, monitored by HPLC).

The reaction system was cooled down to 20° C. and maintained at 20-30° C., to which a solution of sodium methoxide in methanol (8.74 kg of sodium methoxide suspended in 4.80 kg of methanol) was added dropwise. The mixture was stirred for 2 hrs at the same temperature prior to the addition of acetone (49.9 kg) during the course of which solid started to precipitate. The stirring was continued for another 2 hrs. The resultant solid was collected by filtration under reduced pressure, washed with acetone (2.0 kg) and dried at 45-50° C. for 8-13 hrs.

The solid was dissolved in a premixed solvent of DMF-acetone (2.6 kg, acetone:DMF=1.0:0.8, V/V) at 50° C. and stirred for 60 mins at the same temperature. The reaction system was cooled down to 20-30° C. with stirring. The resultant crystals were filtered, washed with acetone (3.2 kg) and dried at 45-50° C. under vacuum for 8-13 hrs to afford 1.77 kg of the entitled compound SGMD-1 as off-white powder. Yield: 87.9%.

Example 5: Preparation of 6-per-deoxy-6-per-(2-carboxyethyl)thio-γ-cyclodextrin Sodium Salt (SGMD)

To a 1 L three-necked flask, DMF (200 g) and 3-mercaptopropionic acid (SM2, 5.76 g) were added successively under an atmosphere of nitrogen. After the reaction system was cooled down to 0-5° C., sodium hydride (7.38 g) was added. The reaction system was maintained and vigorously stirred for 30 mins. Then a solution of SGMD-1 in DMF (10 g of SGMD-1 dissolved in 66.2 g of DMF) was added dropwise over a period of 20-40 mins. Then the reaction system was heated to 70-75° C. and stirred at the same temperature till the SGMD-1 was completely consumed (~12 hrs).

The resultant mixture was cooled down to 20-30° C., to which purified water (96 g) was added and stirred for a further 30 mins at the same temperature. The precipitated solid was filtered, washed with acetone (20 g) and dried at 45±2° C. for 12-15 hrs to afford 8.81 g of the crude product SGMD. Yield: 88.1%.

Example 6: Preparation of 6-per-deoxy-6-per-(2-carboxyethyl)thio-γ-cyclodextrin Sodium Salt To a 1 L three-necked flask, DMF (200 g) and 3-mercaptopropionic acid (SM2, 9.64 g) were added successively under an atmosphere of nitrogen. After the reaction system was cooled down to 0-5° C., sodium hydride (7.38 g) was added. The reaction system was maintained and vigorously stirred for 30 mins. To above reaction mixture was then added dropwise a solution of SGMD-1 in DMF (SGMD-1 (10 g) dissolved in DMF (66.2 g)) over a period of 20-40 mins. Then the reaction system was heated to 70-75° C. and stirred at the same temperature till the SGMD-1 was completely consumed (~12 hrs).

The reaction mixture was cooled down to 20-30° C., to which purified water (96 g) was added and stirred for a further 30 mins. The precipitated solid was filtered, washed with acetone (20 g) and dried at 45±2° C. for 12-15 hrs to afford 8.91 g of the crude product SGMD as solid. Yield: 84.1%.

Example 7: Preparation of 6-per-deoxy-6-per-(2-carboxyethyl)thio-γ-cyclodextrin Sodium Salt To a 1 L three-necked flask, DMF (200 g) and 3-mercaptopropionic acid (SM2, 8.64 g) were added successively under an atmosphere of nitrogen. The reaction system was cooled down to 0-5° C., to which sodium hydride (6.42 g) was added and vigorously stirred for 30 mins. To above reaction mixture was added dropwise a solution of SGMD-1 in DMF (SGMD-1(10 g) dissolved in DMF (66.2 g)) over 20-40 mins. Then the reaction system was heated to 70-75° C. and stirred at the same temperature till the SGMD-1 was completely consumed (~12 hrs).

The reaction mixture was cooled down to 20-30° C., to which purified water (96 g) was added and stirred for a further 30 mins. The precipitated solid was filtered, washed with acetone (20 g) and dried at 45±2° C. for 12-15 hrs to afford 9.02 g of the crude product SGMD as solid. Yield: 90.2%.

Example 8: Preparation of 6-per-deoxy-6-per-(2-carboxyethyl)thio-γ-cyclodextrin Sodium Salt To a 1 L three-necked flask, DMF (200 g) and 3-mercaptopropionic acid (SM2, 8.64 g) were added successively under an atmosphere of nitrogen. The reaction system was cooled down to 0-5° C., to which sodium hydride (4.41 g) was added with vigorous stirring for 30 mins. To above reaction mixture was added dropwise a solution of SGMD-1 in DMF (SGMD-1(10 g) dissolved in DMF (66.2 g)) over 20-40 mins. Then the reaction system was heated to 70-75° C. and stirred at the same temperature till the SGMD-1 was completely consumed (~12 hrs).

The reaction mixture was cooled down to 20-30° C., to which purified water (96 g) was added and stirred for a further 30 mins. The precipitated solid was filtered, washed with acetone (20 g) and dried at 45±2° C. for 12-15 hrs to afford 9.34 g of the crude product SGMD as solid. Yield: 93.4%.

Example 9: Preparation of 6-per-deoxy-6-per-(2-carboxyethyl)thio-γ-cyclodextrin Sodium Salt To a 50 L reaction kettle, DMF (15.88 kg) and 3-mercaptopropionic acid (SM2, 1.05 kg) were added successively under an atmosphere of nitrogen. The reaction system was cooled down to 0-5° C., to which sodium hydride (738 g) was added with vigorous stirring for 30 mins. To above reaction mixture was added dropwise a solution of SGMD-1 in DMF (SGMD-1(1.2 kg) dissolved in DMF (7.94 kg)) over 20-40 mins. Then the reaction system was heated to 70-75° C. and stirred at the same temperature till the SGMD-1 was completely consumed (~12 hrs).

The reaction mixture was cooled down to 20-30° C., to which purified water (3.84 kg) was added and stirred for a further 30 mins. The precipitated solid was filtered, washed with acetone (7.8 kg) and dried at 45±2° C. for 12-15 hrs to afford 1.1 kg of the crude product SGMD as solid. Yield: 91.7%.

Example 10: Preparation of 6-per-deoxy-6-per-(2-carboxyethyl)thio-γ-cyclodextrin Sodium Salt To a 1 L three-necked flask, DMF (200 g) and 3-mercaptopropionic acid (SM2, 5.76 g) were added successively under an atmosphere of nitrogen. The reaction system was cooled down to 0-5° C., to which sodium hydride (4.06 g) was added with vigorous stirring for 30 mins. To above reaction mixture was added dropwise a solution of SGMD-1 in DMF (SGMD-1(10 g) dissolved in DMF (66.2 g)) over 20-40 mins. Then the reaction system was heated to 70-75° C. and stirred at the same temperature till the SGMD-1 was completely consumed (~12 hrs).

The reaction mixture was cooled down to 20-30° C., to which purified water (96 g) was added and stirred for a further 30 mins. The precipitated solid was filtered, washed with acetone (20 g) and dried at 45±2° C. for 12-15 hrs to afford 8.91 g of the crude product SGMD as solid. Yield: 89.1%.

Example 11: Purification of 6-per-deoxy-6-per-(2-carboxyethyl)thio-γ-cyclodextrin Sodium Salt (SGMD)

Figure 3:
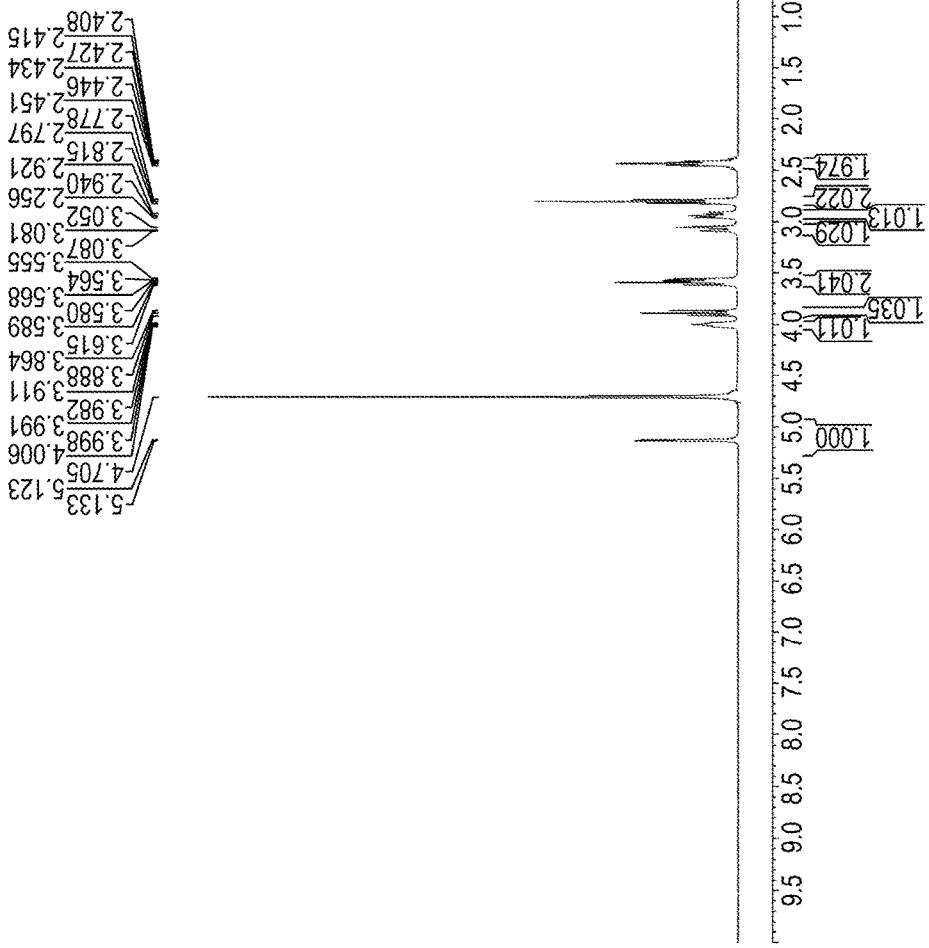
FIG. 3: $^1$H-NMR of 6-per-deoxy-6-per-(2-carboxyethyl)thio-γ-cyclodextrin Sodium Salt.
Figure 4A:
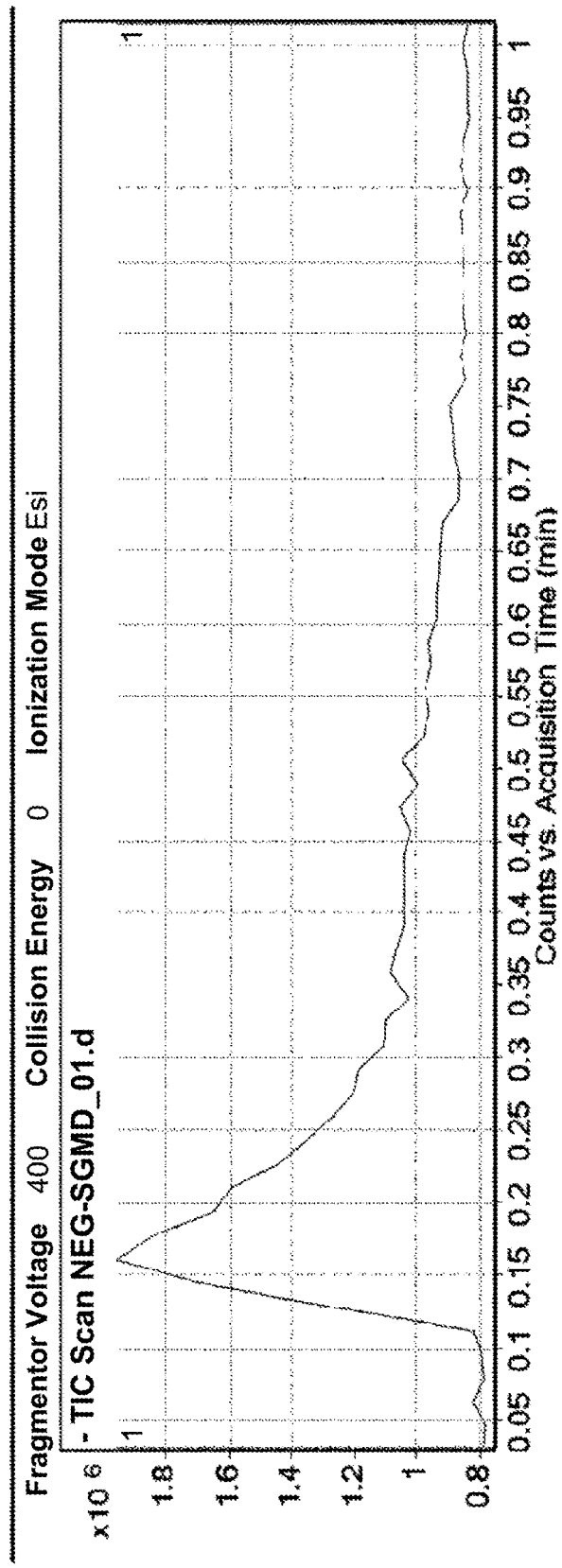
Figure 4B:
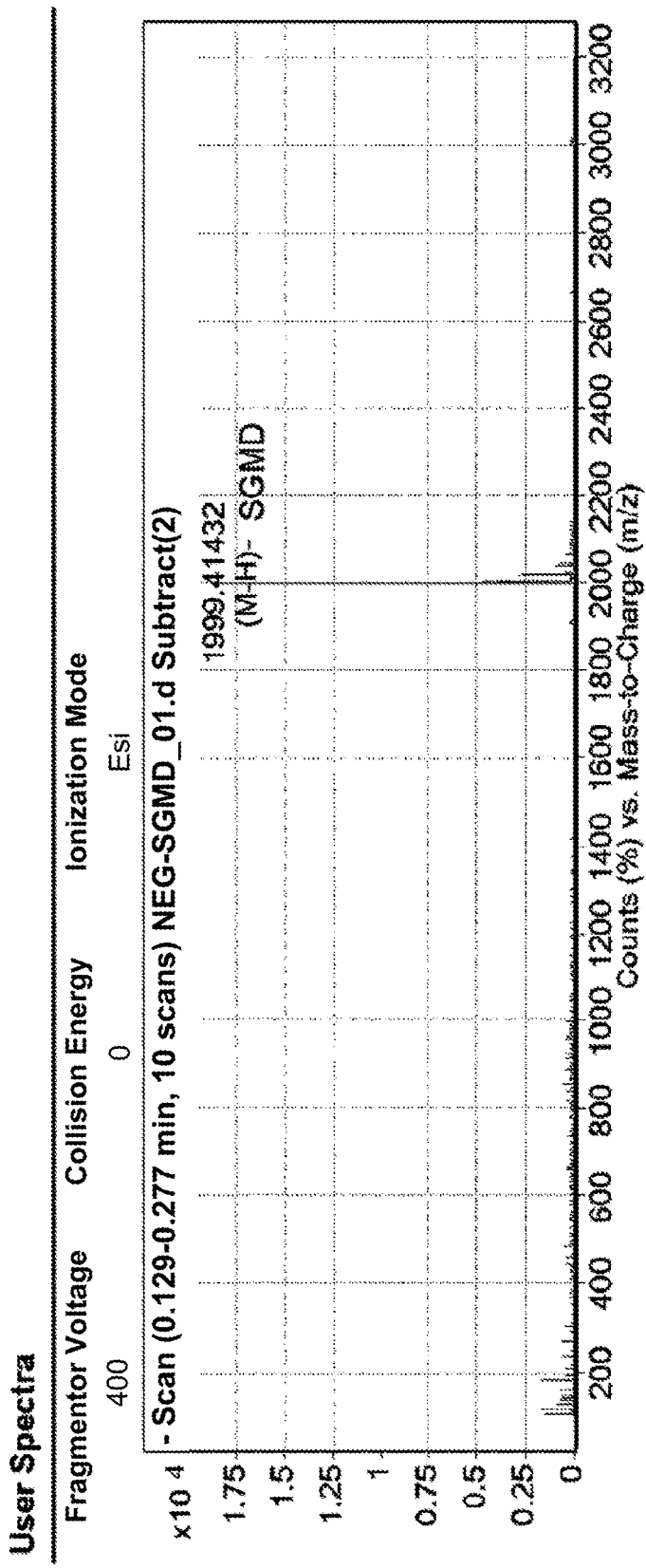

The crude product of SGMD (50 g) was dissolved in a premixed solvent of water (150 g)-methanol (100 g) and heated to 50° C. At this temperature, active carbon (75 g) was added and stirred for 30 mins. After filtering and washing with purified water (50 g), the resultant filtrate was heated to 50-55° C. under the atmosphere of nitrogen, to which methanol (200 g) was added dropwise. After the addition, the reaction system was slowly cooled down to 25-30° C. and stirred at the same temperature for a further 30 mins. The solid was filtered, washed with methanol (100 g) and dried at 60-65° C. for 24 hrs to afford 30.5 g of the pure product (SGMD) as white powder. Yield: 61.0%. $^1$H-NMR (400 MHz, D$_2$O) δ: 5.123-5.133 (d, J=4 Hz, 8H), 3.982-4.006 (m, 8H), 3.864-3.911 (m, 8H), 3.555-3.615 (m, 16H), 3.052-3.087 (m, 8H), 2.921-2.956 (m, 8H), 2.778-2.815 (m, 16H), 2.408-2.451 (in, 16H)(FIG. 3); ESI-HRMS: calcd for [M–H]$^-$ 1999.40159, found 1999.41432, the absolute error is 6.36 ppm and acceptable (FIGS. 4A-4C). Impurity profile of Sugammadex sodium prepared in this example is shown in line SG11, Table 1. The purity of principal peaks is 98.842% (quantitatively by area normalization method). All related substances are acceptable based on the Bridion's acceptance criteria (Shown in Table 1).

Example 12: Purification of 6-per-deoxy-6-per-(2-carboxyethyl)thio-γ-cyclodextrin Sodium Salt The crude SGMD (50 g) was dissolved in a premixed solvent of water (150 g)-ethanol (150 g) and heated to 50° C. Active carbon (10 g) and Al$_2$O$_3$ (50 g) were added and stirred for 30 mins at this temperature. Then the mixture was filtered and the solid cake was washed with purified water (50 g). The resultant filtrate was heated to 50-55° C. under the atmosphere of nitrogen, to which ethanol (200 g) was added dropwise. After the addition, the mixture was slowly cooled to 25-30° C. and stirred for a further 30 mins at the same temperature. The mixture was filtered, washed the solid cake with ethanol (150 g) and dried at 60-65° C. for 24 hrs to afford 27.8 g of the pure product as white powder. Yield: 55.6%. Impurity profile of Sugammadex sodium prepared in this example is shown in line SG12, Table 1. The purity of principal peaks is 98.488% (quantitatively by area normalization method). All related substances are acceptable based on the Bridion's acceptance criteria (Shown in Table 1).

Example 13: Purification of 6-per-deoxy-6-per-(2-carboxyethyl)thio-γ-cyclodextrin Sodium Salt The crude SGMD (50 g) was dissolved in premixed solution of purified water (150 g)-ethanol (150 g) and heated to 50° C., to which Al$_2$O$_3$ (75 g) was added and stirred for 30 mins. Then the mixture was filtered and the solid cake was washed with ethanol (50 g). The resultant filtrate was heated to 50-55° C. under the atmosphere of nitrogen, to which ethanol (400 g) was added dropwise. After addition, the mixture was slowly cooled to 25-30° C. and stirred for a further 30 mins at the same temperature. The precipitate solid was filtered, washed with ethanol (150 g) and dried at 60-65° C. for 24 hrs to afford 23.6 g of entitled SGMD as white powder. Yield: 47.2%. Impurity profile of Sugammadex sodium prepared in this example is shown in line SG13, Table 1. The purity of principal peaks is 98.734% (quantitatively by area normalization method). All related substances are acceptable based on the Bridion's acceptance criteria (Shown in Table 1).

Example 14: Purification of 6-per-deoxy-6-per-(2-carboxyethyl)thio-γ-cyclodextrin Sodium Salt The crude SGMD (50 g) was dissolved in premixed solution of purified water (150 g)-methanol (100 g) and heated to 50° C., to which Al$_2$O$_3$ (60 g) was added and stirred for 30 mins. Then the mixture was filtered and the solid cake was washed with purified water (50 g). The resultant filtrate was heated to 50-55° C. under the atmosphere of nitrogen, to which methanol (200 g) was added dropwise. After addition, the mixture was slowly cooled to 25-30° C. and stirred for a further 30 mins at the same temperature. The precipitate solid was filtered, washed with methanol (100 g) and dried at 60-65° C. for 24 hrs to afford 35.1 g of entitled SGMD as white powder. Yield: 70.2%. Impurity profile of Sugammadex sodium prepared in this example is shown in line SG14, Table 1. The purity of principal peaks is 98.790% (quantitatively by area normalization method). All related substances are acceptable based on the Bridion's acceptance criteria (Shown in Table 1).

Example 15: Purification of 6-per-deoxy-6-per-(2-carboxyethyl)thio-γ-cyclodextrin Sodium Salt The crude SGMD (50 g) was dissolved in premixed solution of purified water (150 g)-methanol (150 g) and heated to 50° C., to which active carbon (40 g) was added and stirred for 30 mins. Then the mixture was filtered and the solid cake was washed with purified water (50 g). The resultant filtrate was heated to 50-55° C. under the atmosphere of nitrogen, to which methanol (200 g) was added dropwise. After addition, the mixture was slowly cooled to 25-30° C. and stirred for a further 30 mins at the same temperature. The precipitate solid was filtered, washed with methanol (100 g) and dried at 60-65° C. for 24 hrs to afford 31.6 g of entitled SGMD as white powder. Yield: 63.2%. Impurity profile of Sugammadex sodium prepared in this example is shown in line SG15, Table 1. The purity of principal peaks is 98.884% (quantitatively by area normalization method). All related substances are acceptable based on the Bridion's acceptance criteria (Shown in Table 1).

Example 16: Purification of 6-per-deoxy-6-per-(2-carboxyethyl)thio-γ-cyclodextrin Sodium Salt The crude SGMD (50 g) was dissolved in premixed solution of purified water (150 g)-methanol (100 g) and heated to 50° C., to which active carbon (10 g) and neutral Al$_2$O$_3$ (65 g) were added and stirred for 30 mins. Then the mixture was filtered and the solid cake was washed with purified water (50 g). The resultant filtrate was heated to 50-55° C. under the atmosphere of nitrogen, to which methanol (200 g) was added dropwise. After addition, the mixture was slowly cooled to 25-30° C. and stirred for a further 30 mins at the same temperature. The precipitate solid was filtered, washed with methanol (100 g) and dried at 60-65° C. for 24 hrs to afford 34.5 g of entitled SGMD as white powder. Yield: 69.0%. Impurity profile of Sugammadex sodium prepared in this example is shown in line SG16, Table 1. The purity of principal peaks is 98.833% (quantitatively by area normalization method). All related substances are acceptable based on the Bridion's acceptance criteria (Shown in Table 1).

Example 17: Purification of 6-per-deoxy-6-per-(2-carboxyethyl)thio-γ-cyclodextrin Sodium Salt The crude SGMD (50 g) was dissolved in a premix of water (150 g)-methanol (100 g) and heated to 50° C., to which active carbon (10 g) was added and stirred for 30 mins. Then the active carbon was filtered and washed with purified water (50 g). The resultant filtrate was heated to 50-55° C. under the atmosphere of nitrogen, to which methanol (200 g) was added dropwise. After addition, the mixture was slowly cooled to 25-30° C. and stirred for a further 30 mins at the same temperature. The precipitate was filtered, washed with methanol (100 g) and dried at 60-65° C. for 24 hrs to afford 36.2 g of entitled product as white powder. Yield: 72.4%. Impurity profile of Sugammadex sodium prepared in this example is shown in line SG17, Table 1. The purity of principal peaks is 98.878% (quantitatively by area normalization method). All related substances are acceptable based on the Bridion's acceptance criteria (Shown in Table 1).

Example 18: Purification of 6-per-deoxy-6-per-(2-carboxyethyl)thio-γ-cyclodextrin Sodium Salt The crude SGMD 50 g was dissolved in a premix solution of water (150 g)-methanol (100 g) and heated to 50° C., to which active carbon (20 g) and neutral Al$_2$O$_3$ (40 g) were added and stirred for 30 mins. Then the mixture was filtered and the solid cake was washed with purified water (50 g). The resultant filtrate was heated to 50-55° C. under the atmosphere of nitrogen, to which methanol (200 g) was added dropwise. After addition, the mixture was slowly cooled to 25-30° C. and stirred for a further 30 mins. The mixture was filtered, washed with methanol (100 g) and dried at 60-65° C. for 24 hrs to afford 33.4 g of title product as white powder. Yield: 66.8%. Impurity profile of Sugammadex sodium prepared in this example is shown in line SG18, Table 1. The purity of principal peaks is 98.783% (quantitatively by area normalization method). All related substances are acceptable based on the Bridion's acceptance criteria (Shown in Table 1).

Example 19: Purification of 6-per-deoxy-6-per-(2-carboxyethyl)thio-γ-cyclodextrin Sodium Salt The crude SGMD (50 g) was dissolved in a premix solution (water (150 g)-ethanol (150 g)) and heated to 50° C., to which neutral Al$_2$O$_3$ (25 g) was added and stirred for 30 mins. Then the mixture was filtered and the solid cake was washed with purified water (50 g). The resultant filtrate was heated to 50-55° C. under the atmosphere of nitrogen, to which ethanol (200 g) was added dropwise. After addition, the mixture was slowly cooled to 25-30° C. and stirred for a further 30 mins. The mixture was filtered, washed with ethanol (150 g) and dried at 60-65° C. for 24 hrs to afford 43.3 g of title product as white powder. Yield: 86.6%. Impurity profile of Sugammadex sodium prepared in this example is shown in line SG19, Table 1. The purity of principal peaks is 99.269% (quantitatively by area normalization method). All related substances are acceptable based on the Bridion's acceptance criteria (Shown in Table 1).

Figure 5A:
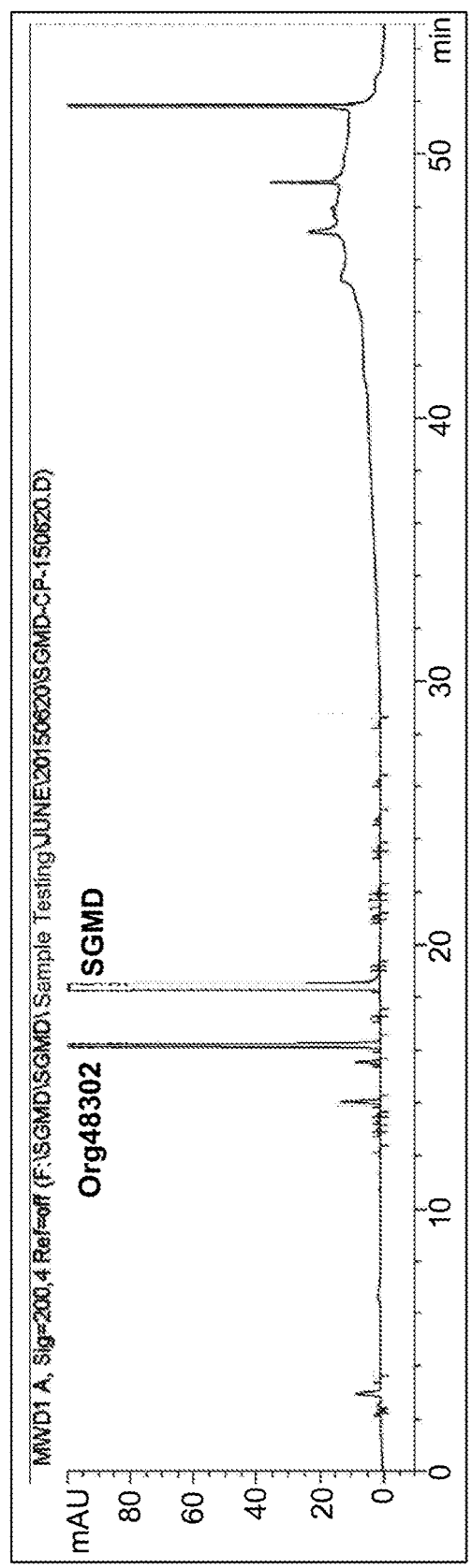
Figure 6A:
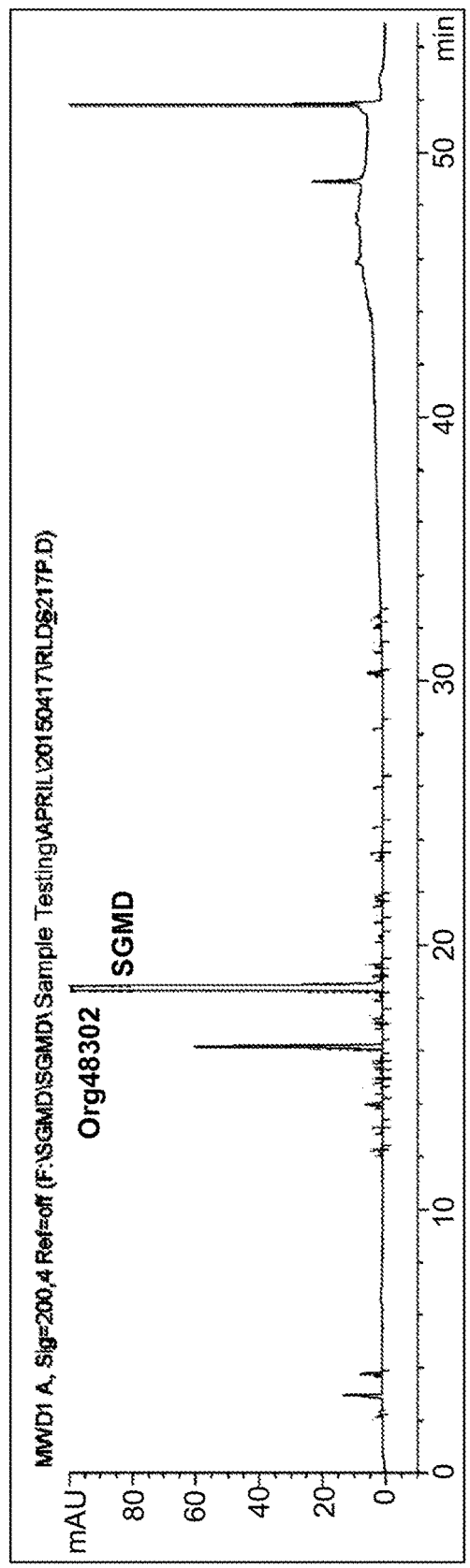
Figure 7A:
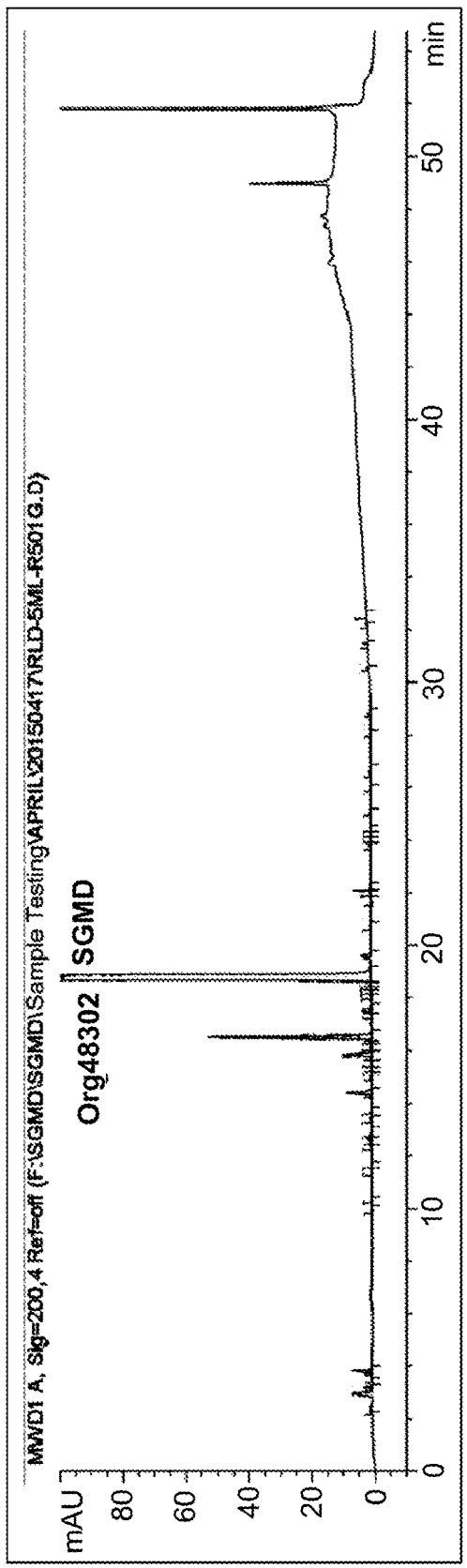
Figure 8A:
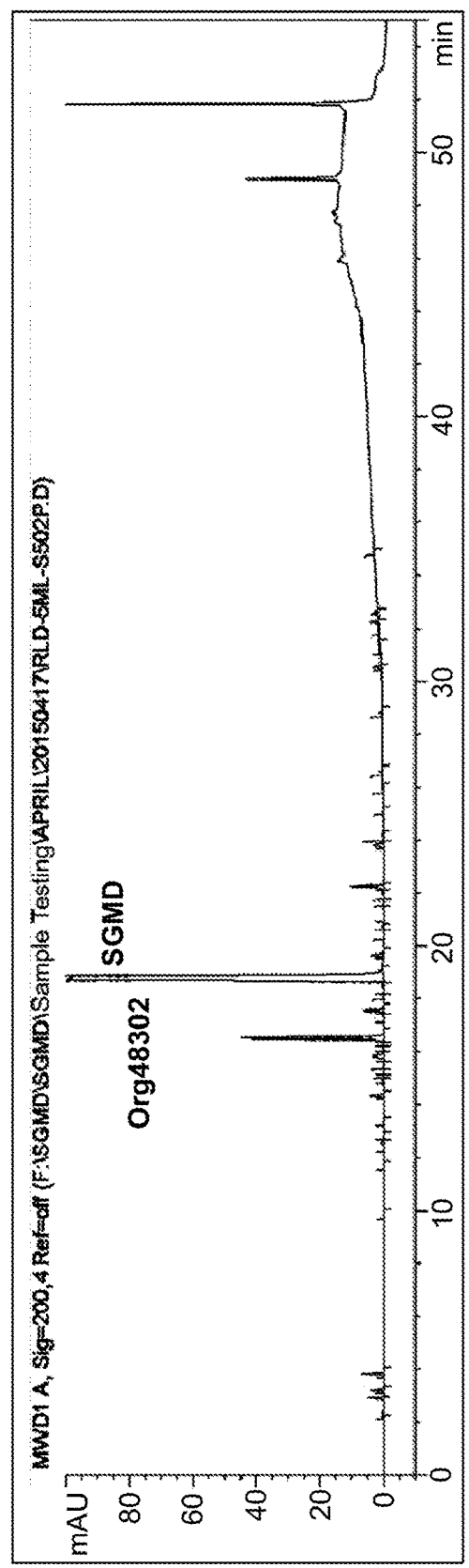

Example 20: Purification of 6-per-deoxy-6-per-(2-carboxyethyl)thio-γ-cyclodextrin Sodium Salt The crude SGMD (1.5 kg) was dissolved in a premix solution (water (4.5 kg)-methanol (3.0 kg)) and heated to 50° C., to which active carbon (300 g) and neutral Al$_2$O$_3$ (750 g) were added and stirred for 30 mins. Then the mixture was filtered and the solid cake was washed with purified water (1.5 kg). The resultant filtrate was heated to 50-55° C. under the atmosphere of nitrogen, to which methanol (6.0 kg) was added dropwise. After addition, the mixture was slowly cooled to 25-30° C. and stirred for a further 30 mins. The mixture was filtered, washed with methanol (3.0 kg) and dried at 60-65° C. for 24 hrs to afford 0.95 kg title product as white powder. Yield: 63.3%. Impurity profile of Sugammadex sodium prepared in this example are shown in line SG20, Table 1 (FIGS. 5A-5C, The detection of impurities can refer to the section "Impurity Analysis of Sugammadex sodium salt prepared by this process and reference listed drug (Bridion)"). The purity of principal peaks is 98.796% (quantitatively by area normalization method). All related substances are acceptable based on the Bridion's acceptance criteria (Shown in Table 1).

Example 21: Purification of 6-per-deoxy-6-per-(2-carboxyethyl)thio-γ-cyclodextrin Sodium Salt The crude SGMD (1.5 kg) was dissolved in a premix solution of water (4.5 kg)-ethanol (4.5 kg) and heated to 50° C., to which active carbon (150 g) and neutral Al$_2$O$_3$ (2.25 kg) were added and stirred at this temperature for 30 mins. Then the mixture was filtered and the solid cake was washed with purified water (1.5 kg). The resultant filtrate was heated to 50-55° C. under the atmosphere of nitrogen, to which ethanol (9 kg) was added dropwise at the same temperature. After addition, the reaction system was slowly cooled to 25-30° C. and stirred for a further 30 mins. The mixture was filtered, washed with ethanol (3 kg) and dried at 60-65° C. for 24 hrs to afford 1.08 kg of entitled product as white powder. Yield: 72.0%. Impurity profile of Sugammadex sodium prepared in this example is shown in line SG21, Table 1. The purity of principal peaks is 98.916% (quantitatively by area normalization method). All related substances are acceptable based on the Bridion's acceptance criteria (Shown in Table 1).

Example 22: Preparation of 6-per-deoxy-6-per-iodo-γ-cyclodextrin

To a 500 L reactor, triphenylphosphine (36.1 kg) was added to DMF (132 kg) at room temperature under nitrogen. To this mixture was added dropwise a solution of iodine (36.7 kg) in DMF (45 kg). After addition, the reaction mixture was stirred at 20-30° C. for 30 mins. γ-cyclodextrin (12.0 kg) was then added and the mixture was heated to 70° C. for 24 hrs until the reaction was completed (HPLC detected).

The mixture was allowed to cool to 20° C., to which sodium methoxide (8.7 kg sodium methoxide in 48.0 kg methanol) was added at 20-30° C. and the mixture was stirred for 2 hrs at the same temperature. Acetone (499 kg) was added at 20-30° C. and the mixture was stirred for 2 hrs, then the solid was collected by filtration and washed with acetone (20 kg), dried at 45-50° C. for 8-13 hrs.

The solid was dissolved in the solution of DMF and acetone (26 kg, acetone:DMF=1.0:0.8, V/V) at 50° C. and stirred for 60 mins at the same temperature. The mixture was allowed to cool to 20-30° C. and stirred, crystallized, filtered and washed with 32 kg acetone, then dried at 45-50° C. for 8-13 hrs to obtain 17.2 kg white powder, yield: 85.6%.

Example 23: Preparation of 6-per-deoxy-6-per-iodo-γ-cyclodextrin

To a 1000 L reactor, triphenylphosphine (72.2 kg) was added to DMF (264 kg) at room temperature under nitrogen. To this mixture was added dropwise a solution of iodine (73.4 kg) in DMF (90 kg). After addition, the reaction mixture was stirred at 20-30° C. for 30 mins. γ-cyclodextrin (24.0 kg) was then added and the mixture was heated to 70° C. for 24 hrs until the reaction was completed (HPLC detected).

The mixture was allowed to cool to 20° C., to which sodium methoxide (17.4 kg sodium methoxide in 96.0 kg methanol) was added at 20-30° C. and the mixture was stirred for 2 hrs at the same temperature. Acetone (1000 kg) was added at 20-30° C. and the mixture was stirred for 2 hrs, then the solid was collected by filtration and washed with acetone (40 kg), dried at 45-50° C. for 8-13 hrs.

The solid was dissolved in the solution of DMF and acetone (52 kg, acetone/DMF=1.0:0.8, V/V) at 50° C. and stirred for 60 mins at the same temperature. The mixture was allowed to cool to 20-30° C. and stirred, crystallized, filtered and washed with 64 kg acetone, then dried at 45-50° C. for 8-13 hrs to obtain 34.6 kg white powder, yield: 86.1%.

Example 24: Preparation of 6-per-deoxy-6-per-(2-carboxyethyl)thio-γ-cyclodextrin Sodium Salt To a 500 L reactor, 3-mercaptopropionic acid (10.5 kg) was dissolved in DMF (158.8 kg) at room temperature under nitrogen. To this solution was added sodium hydride (7.7 kg) at 0-5° C. and the mixture was stirred for a further 30 mins. To this mixture was then added dropwise a solution of 6-per-deoxy-6-per-iodo-γ-cyclodextrin (12.0 kg) in DMF (79.4 kg) in 20-40 mins. After addition, the reaction mixture was heated at 70-75° C. for 12 hrs until the reaction was completed.

After cooling to 20-30° C., water (38.4 kg) was added to the mixture and stirred for 30 mins, the resulting solid was filtered and washed with 78 kg acetone, then dried at 45±2° C. for 12-15 hrs to obtain 11.6 kg solid, yield: 96.7%.

Example 25: Preparation of 6-per-deoxy-6-per-(2-carboxyethyl)thio-γ-cyclodextrin Sodium Salt (SGMD)

To a 1000 L reactor, 3-mercaptopropionic acid (21.0 kg) was dissolved in DMF (317.6 kg) at room temperature under nitrogen. To this solution was added sodium hydride (15.4 kg) at 0-5° C. and the mixture was stirred for a further 30 mins. To this mixture was then added dropwise a solution of 6-per-deoxy-6-per-iodo-γ-cyclodextrin (24.0 kg) in DMF (158.8 kg) in 20-40 mins. After addition, the reaction mixture was heated at 70-75° C. for 12 hrs until the reaction was completed.

After cooling to 20-30° C., water (76.8 kg) was added to the mixture and stirred for 30 mins, the resulting solid was filtered and washed with 156 kg acetone, then dried at 45±2° C. for 12-15 hrs to obtain 23.0 kg crude SGMD, yield: 95.8%.

Figure 9A:
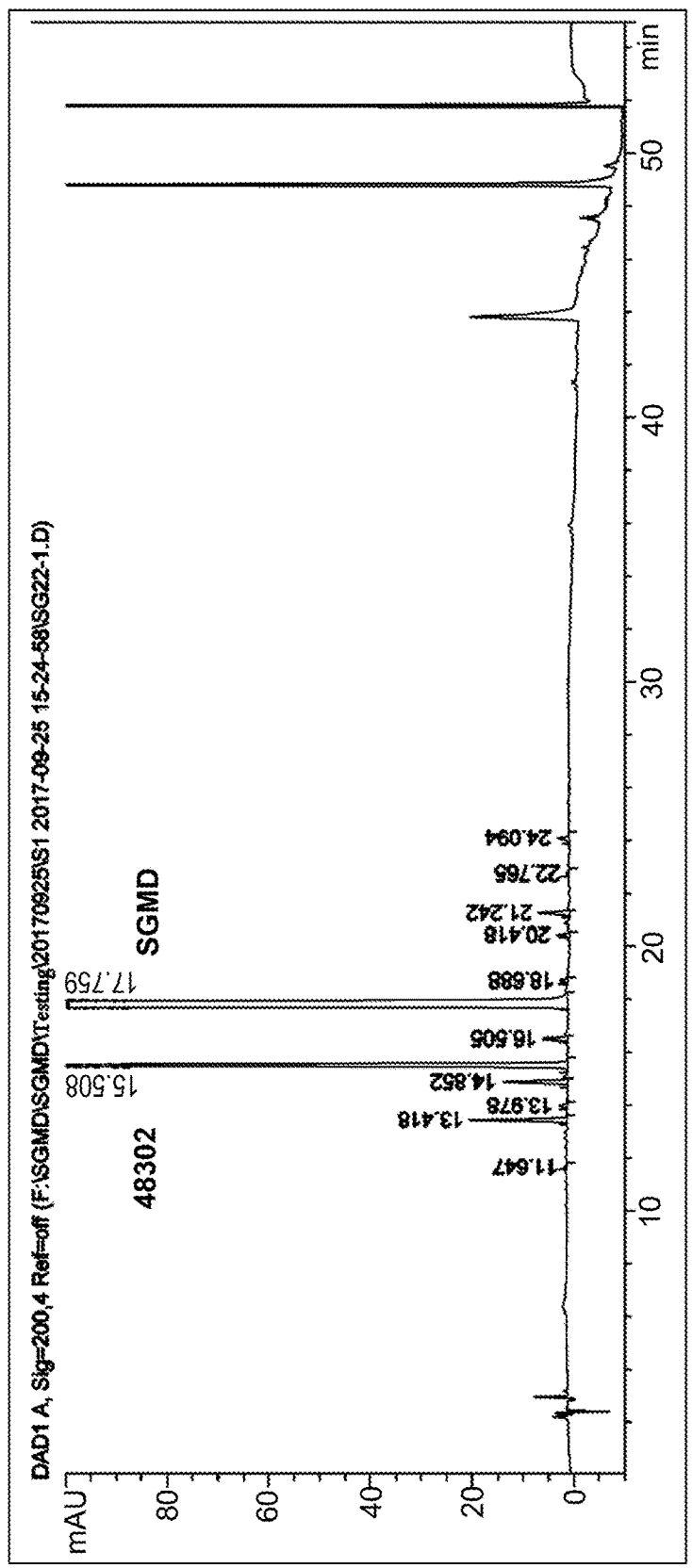

Example 26: Purification of 6-per-deoxy-6-per-(2-carboxyethyl)thio-γ-cyclodextrin Sodium Salt The crude SGMD 10.0 kg was dissolved in water (30 kg) and methanol (20 kg), treated with activated carbon (2.0 kg) and neutral $Al_2O_3$ (5.0 kg) at 50° C. for 30 mins. After filtering and washing with purified water (10.0 kg), the filtrate was heated to 50-55° C. under nitrogen and added methanol (40 kg) dropwise at the same temperature. After addition, the reaction system was slowly cooled to 25-30☐ and stirred for 30 mins at the same temperature. The mixture was filtered and washed with 20 kg methanol, then dried at 60-65° C. for 24 hrs to obtain 6.3 kg white powder, yield: 63.0% (FIGS. 9A-9B). Impurity profile of Sugammadex sodium prepared in this example is shown in line SG22, Table 1. The purity of principal peaks is 98.362% (quantitatively by area normalization method). The detected impurities are less than those of the commercial injections and the contents of the impurities are lower than those of the corresponding impurities contained in the commercial injections.

Figure 10A:
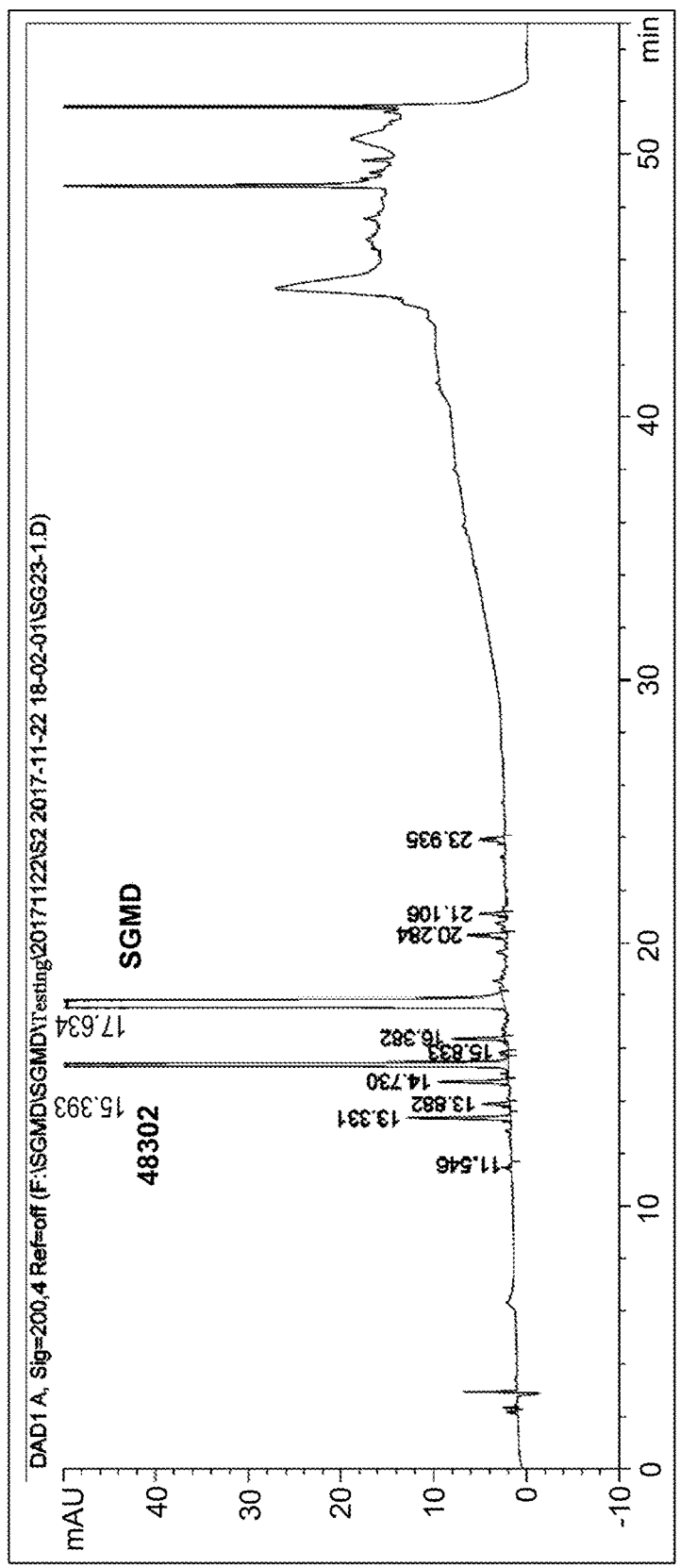

Example 27: Purification of 6-per-deoxy-6-per-(2-carboxyethyl)thio-γ-cyclodextrin Sodium Salt The crude SGMD 13.5 kg was dissolved in purified water (40.5 kg) and methanol (27 kg), treated with activated carbon (2.7 kg) and neutral $Al_2O_3$ (6.8 kg) at 50° C. for 30 mins. After filtering and washing with purified water (13.5 kg), the filtrate was heated to 50-55° C. under nitrogen and added methanol (54 kg) dropwise at the same temperature. After addition, the reaction system was slowly cooled to 25-30☐ and stirred for 30 mins at the same temperature. The mixture was filtered and washed with 27 kg methanol, then dried at 60-65° C. for 24 hrs to obtain 8.3 kg white powder, yield: 61.5% (FIGS. 10A-10B). Impurity profile of Sugammadex sodium prepared in this example is shown in line SG23, Table 1. The purity of principal peaks is 98.808% (quantitatively by area normalization method). The detected impurities are less than those of the commercial injections and the contents of the impurities are lower than those of the corresponding impurities contained in the commercial injections.

Figure 11A:
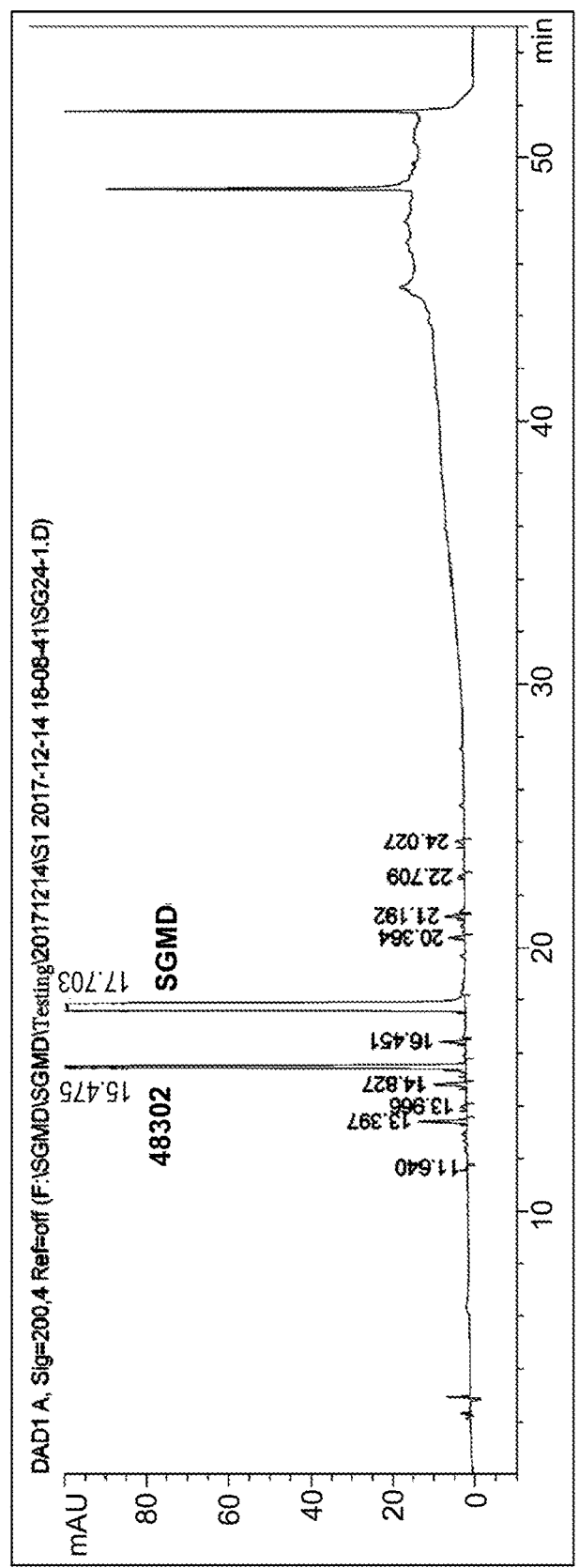

Example 28: Purification of 6-per-deoxy-6-per-(2-carboxyethyl)thio-γ-cyclodextrin Sodium Salt The crude SGMD 12.0 kg was dissolved in purified water (36 kg) and ethanol (36 kg), treated with activated carbon (1.2 kg) and neutral $Al_2O_3$ (18 kg) at 50° C. for 30 mins. After filtering and washing with purified water (12 kg), the filtrate was heated to 50-55° C. under nitrogen and added ethanol (72 kg) dropwise at the same temperature. After addition, the reaction system was slowly cooled to 25-30 ☐ and stirred for 30 mins at the same temperature. The mixture was filtered and washed with 24 kg ethanol, then dried at 60-65° C. for 24 hrs to obtain 8.5 kg white powder, yield: 70.8% (FIGS. 11A-11B). Impurity profile of Sugammadex sodium prepared in this example is shown in line SG24, Table 1. The purity of principal peaks is 98.732% (quantitatively by area normalization method). The detected impurities are less than those of the commercial injections and the contents of the impurities are lower than those of the corresponding impurities contained in the commercial injection.

Impurity Analysis of Sugammadex Sodium Salt Prepared by this Process and Reference Listed Drug (Bridion).

Impurities or by-products introduced in the manufacture process of Sugammadex sodium have similar chemical structures and polarities with Sugammadex sodium (SGMD). The UV absorption of these impurities is the same or similar with SGMD. Therefore, in the early stage of process optimization, amount of impurities in BRIDION and SGMD prepared in examples 11 to 21 was calculated by area normalization method according to Chinese Pharmacopoeia 2015 in the case of reference substances of impurities were not available, respectively.

Sample Preparation

Preparation of Test Samples:

(1) Test solution of Sugammadex sodium: Transfer an accurately weighed quantity of Sugammadex sodium salt prepared in examples 11-21 and 26-28 to a 10 ml volumetric flask and dilute with purified water to a concentration of about 2.0 mg of Sugammadex sodium per mL. The prepared test solutions are mixed prior to test (abbreviated as SG11, SG12, SG13, SG14, SG15, SG16, SG17, SG18, SG19, SG20, SG21, SG22, SG23 and SG24, respectively).

(2) Test solution of Reference Listed Drug (Bridion): Transfer 1.0 ml of the Reference Listed Drug (Bridion purchased from Japan MSD Corporation, batch number: S217P, S502P and R501G, concentration: 100 mg/ml) to a 50 ml volumetric flask and dilute with purified water to a concentration of about 2.0 mg of Bridon per mL.

Sample Analysis:

Agilent 1260 high performance liquid chromatograph (HPLC) system (purchased from Agilent Technologies, equipped with UV detector, column thermostat and autosampler) is used.

Based on Chinese Pharmacopoeia 2015, gradient elution is performed using HPLC system, wherein column is filled with octadecyl silane bonded silica gel, the detection wavelength is 200 nm, the flow rate is 0.5 mL per minute, and the column temperature is set to 40° C., the mobile phases are as follows:

Solution A: Buffer: acetonitrile (83:20, V/V), wherein buffer is 25 mM sodium dihydrogen phosphate solution with pH of 3.0 which is adjusted with phosphoric acid, Solution B: Acetonitrile The gradients used in the detection are as follows:

| | T (min) | | | | | | | | | |
|---|---|---|---|---|---|---|---|---|---|---|
| | 0 | 5 | 15 | 22 | 27 | 32 | 37 | 42 | 42.01 | 52 |
| B (%) | 0 | 0 | 2 | 8 | 25 | 50 | 70 | 70 | 0 | 0 |
| A (%) | 100 | 100 | 98 | 92 | 75 | 50 | 30 | 30 | 100 | 100 |

The relative retention time (RRT) is used to fix the positions of the impurities and the principal components. In the liquid chromatograph traces of the test solution of Reference Listed Drug (Bridion) and Sugammadex sodium prepared in the present invention, the peaks of which the RRTs are 0.88 and 1.00 are Org48302 and Sugammadex sodium respectively. Org48302 is regarded as a principal component too. Results of the above analysis have been summarized in Table 1. In the three batches of the Reference Listed Drug (Bridion), the purity of the two principal components by area normalized method is about 97.0%; the number of detected impurities is greater than that in the sample product prepared following the process described in this invention. The spectra of the three batches of Reference Listed Drug (Bridion) are shown in FIGS. 6A-6C to 8A-8C.

It is to be illustrated that all documents mentioned in the present invention are incorporated by reference as if each individual document is individually incorporated by reference. In addition, it is to be understood that the invention has been described with reference to specific embodiments thereof and the principles of the invention, and that various changes and modifications may be effected therein by one skilled in the art without departing from the scope of the invention spirit, and scope of the invention, which equivalents fall within the scope of the invention.

TABLE 1

Comparison of the Impurities of Sugammadex Sodium Prepared by Different Process

| Name of Sample | The normalized content of Impurities and Principal Component (%) | | | | | | | | | | | | | | | | |
|---|---|---|---|---|---|---|---|---|---|---|---|---|---|---|---|---|---|
| 名称 | 0.17 | 0.21 | 0.66 | 0.76 | 0.84 | 0.88 | 0.94 | 0.98 | 1.00 | 1.03 | 1.05 | 1.11 | 1.19 | 1.72 | 1.53 | 1.65 | 1.75 |
| S217P | — | 0.304 | 0.085 | 0.326 | 0.362 | 3.544 | 0.468 | 0.048 | 93.424 | 0.046 | 0.301 | 0.066 | 0.221 | 0.069 | — | 0.208 | 0.070 |
| R501G | 0.108 | 0.315 | 0.010 | 0.478 | 0.546 | 3.184 | 0.264 | 0.022 | 93.777 | 0.195 | 0.030 | 0.153 | 0.059 | 0.058 | — | 0.047 | 0.060 |
| S502P | 0.168 | 0.311 | 0.077 | 0.260 | 0.293 | 2.706 | 0.351 | 0.046 | 94.341 | 0.215 | 0.039 | 0.198 | — | 0.181 | 0.551 | 0.105 | 0.114 |
| SG 11 | — | — | — | 0.367 | 0.238 | 4.365 | — | 0.012 | 94.477 | 0.028 | — | 0.078 | 0.047 | — | — | — | — |
| SG 12 | — | — | 0.024 | 0.377 | 0.506 | 3.608 | — | 0.047 | 94.840 | 0.022 | 0.029 | — | 0.063 | 0.046 | 0.068 | 0.065 | — |
| SG 13 | — | — | 0.014 | 0.369 | 0.239 | 4.389 | — | 0.035 | 94.345 | 0.018 | 0.010 | — | 0.080 | — | 0.048 | 0.024 | 0.064 |
| SG 14 | — | — | — | 0.367 | 0.237 | 4.389 | — | 0.032 | 94.401 | 0.012 | 0.013 | 0.080 | 0.046 | 0.047 | — | — | — |
| SG 15 | — | — | 0.012 | 0.369 | 0.240 | 4.321 | — | 0.026 | 94.563 | 0.022 | 0.015 | 0.082 | 0.049 | 0.054 | — | — | — |
| SG 16 | — | — | — | 0.367 | 0.245 | 4.323 | — | 0.025 | 94.510 | 0.018 | 0.033 | 0.084 | 0.053 | 0.049 | — | — | — |
| SG 17 | — | — | — | 0.366 | 0.243 | 4.312 | — | 0.020 | 94.566 | 0.024 | 0.014 | 0.080 | 0.053 | 0.047 | — | — | — |
| SG 18 | — | — | — | 0.368 | 0.239 | 4.394 | — | 0.027 | 94.389 | 0.019 | 0.013 | 0.079 | 0.047 | 0.055 | — | — | — |
| SG 19 | — | — | 0.014 | 0.356 | 0.234 | 4.395 | — | 0.031 | 94.874 | 0.036 | 0.012 | 0.087 | 0.070 | 0.054 | — | — | — |
| SG 20 | — | 0.012 | 0.013 | 0.377 | 0.232 | 4.759 | — | — | 94.037 | 0.015 | 0.019 | 0.077 | 0.032 | 0.073 | — | — | — |
| SG 21 | — | — | — | 0.353 | 0.210 | 4.473 | — | — | 94.443 | 0.017 | 0.020 | 0.068 | 0.021 | 0.086 | 0.055 | — | — |
| SG 22 | — | — | 0.022 | 0.577 | 0.411 | 4.765 | 0.137 | — | 93.596 | — | 0.048 | 0.081 | 0.199 | — | — | — | — |
| SG 23 | — | — | 0.013 | 0.341 | 0.237 | 3.139 | 0.161 | — | 95.669 | — | — | 0.135 | 0.089 | — | — | — | — |
| SG 24 | — | — | 0.012 | 0.362 | 0.257 | 5.011 | 0.176 | — | 93.721 | — | — | 0.120 | 0.159 | — | — | — | — |

Note:
Impurities with content less than 0.05% are ignored.

We claim:

1. A process for the preparation of 6-per-deoxy-6-per-(2-carboxyethyl)thio-γ-cyclodextrin sodium salt, the process comprising the steps of:
reacting γ-cyclodextrin (SM1) with iodine in the presence of triphenylphosphine in an organic solvent to afford an intermediate, 6-per-deoxy-6-iodo-γ-cyclodextrin (SGMD-1);
adding methanol solution of sodium methoxide into the reaction system followed by the addition of acetone without removal of the solvents under reduced pressure to obtain the crude product of SGMD-1 as a solid after filtration;
purifying the crude SGMD-1 by recrystallization;
reacting thus obtained recrystallized intermediate (SGMD-1) with 3-mercaptopropionic acid (SM2) in basic medium, to obtain a crude product of 6-per-deoxy-6-per-(2-carboxyethyl)thio-γ-cyclodextrin sodium salt (SGMD);
purifying the crude SGMD by passing through adsorbent(s) followed by recrystallization.

2. The process according to claim 1, wherein the organic solvent is N,N-dimethylformamide (DMF).

3. The process according to claim 1, wherein the ratio (V/W) of acetone and γ-cyclodextrin (SM1) is 30:1-150:1.

4. The process according to claim 1, wherein the solvents used in the recrystallization of crude SGMD-1 are N,N-dimethylformamide, dimethyl sulfoxide (DMSO), methanol, ethanol, isopropanol or acetone or a mixture of two of the above solvents.

5. The process according to claim 4, wherein the ratio (V/V) of acetone/DMF is 1:0.3-1:2.5.

6. The process according to claim 1, wherein the molar ratio of SGMD-1 and 3-mercaptopropionic acid (SM2) is 1:8-1:25.

7. The process according to claim 1, wherein the molar ratio of SGMD-1 and sodium hydride is 1:10-1:50.

8. The process according to claim 1, wherein the solvents used in the recrystallization of crude SGMD are ethanol, water, methanol or isopropanol or a mixture of water and one selected from the group consisting of ethanol, methanol, and isopropanol.

9. The process according to claim 1, wherein the adsorbent(s) is selected from the group consisting of active carbon, silica gel, macroporous resin, aluminum oxide, molecular sieves and zeolite.

10. The process according to claim 1, wherein the ratio (W/W) of crude SGMD and adsorbent(s) is 1:0.1-1:2.5.

11. The process according to claim 1, wherein the basic medium is sodium hydride.

12. The process according to claim 1, wherein the ratio (V/W) of acetone and γ-cyclodextrin (SM1) is 35:1-140:1.

13. The process according to claim 1, wherein the ratio (V/W) of acetone and γ-cyclodextrin (SM1) is 40:1-130:1.

14. The process according to claim 1, wherein the ratio (V/W) of acetone and γ-cyclodextrin (SM1) is 45:1-120:1.

15. The process according to claim 1, wherein the ratio (V/W) of acetone and γ-cyclodextrin (SM1) is 50:1-110:1.

16. The process according to claim 1, wherein the ratio (V/W) of acetone and γ-cyclodextrin (SM1) is 50:1-100:1.

17. The process according to claim 1, wherein the ratio (V/W) of acetone and γ-cyclodextrin (SM1) is 60:1-100:1.

18. The process according to claim 4, wherein the solvents used in the recrystallization of crude SGMD-1 are a mixture of acetone and DMF, a mixture of acetone and DMSO, a mixture of methanol and DMF, a mixture of ethanol and DMF, or a mixture of acetone and DMF.

19. The process according to claim 4, wherein the ratio (V/V) of acetone/DMF is 1:0.4-1:2.4.

20. The process according to claim 4, wherein the ratio (V/V) of acetone/DMF is 1:0.5-1:2.3.

21. The process according to claim 4, wherein the ratio (V/V) of acetone/DMF is 1:0.6-1:2.2.

22. The process according to claim 4, wherein the ratio (V/V) of acetone/DMF is 1:0.7-1:2.1.

23. The process according to claim 4, wherein the ratio (V/V) of acetone/DMF is 1:0.8-1:2.0.

24. The process according to claim 1, wherein the molar ratio of SGMD-1 and 3-mercaptopropionic acid (SM2) is 1:9-1:24.

25. The process according to claim 1, wherein the molar ratio of SGMD-1 and 3-mercaptopropionic acid (SM2) is 1:10-1:22.

26. The process according to claim 1, wherein the molar ratio of SGMD-1 and 3-mercaptopropionic acid (SM2) is 1:11-1:21.

27. The process according to claim 1, wherein the molar ratio of SGMD-1 and 3-mercaptopropionic acid (SM2) is 1:12-1:20.

28. The process according to claim 11, wherein the molar ratio of SGMD-1 and sodium hydride is 1:12-1:48.

29. The process according to claim 11, wherein the molar ratio of SGMD-1 and sodium hydride is 1:15-1:45.

30. The process according to claim 11, wherein the molar ratio of SGMD-1 and sodium hydride is 1:17-1:42.

31. The process according to claim 11, wherein the molar ratio of SGMD-1 and sodium hydride is 1:18-1:40.

32. The process according to claim 11, wherein the molar ratio of SGMD-1 and sodium hydride is 1:22-1:40.

33. The process according to claim 8, wherein the solvents used in the recrystallization of crude SGMD is a mixture of methanol and water or a mixture of ethanol and water.

34. The process according to claim 9, wherein the adsorbent(s) is aluminum oxide or activated carbon, or a mixture thereof.

35. The process according to claim 34, wherein the aluminum oxide is basic aluminum oxide or neutral aluminum oxide.

36. The process according to claim 1, wherein the ratio (W/W) of crude SGMD and adsorbent(s) is 1:0.1-1:2.3.

37. The process according to claim 1, wherein the ratio (W/W) of crude SGMD and adsorbent(s) is 1:0.1-1:2.1.

38. The process according to claim 1, wherein the ratio (W/W) of crude SGMD and adsorbent(s) is 1:0.2-1:2.0.

39. The process according to claim 1, wherein the ratio (W/W) of crude SGMD and adsorbent(s) is 1:0.2-1:1.8.

40. The process according to claim 1, wherein the ratio (W/W) of crude SGMD and adsorbent(s) is 1:0.2-1:1.5.

* * * * *